US012611301B2

(12) United States Patent
Yushtein et al.

(10) Patent No.: US 12,611,301 B2
(45) Date of Patent: Apr. 28, 2026

(54) COMMISSURE LOCKING MEMBER

(71) Applicant: EDWARDS LIFESCIENCES CORPORATION, Irvine, CA (US)

(72) Inventors: Haim Yushtein, Netanya (IL); Noam Nir, Pardes-Hanna (IL); Michael Bukin, Pardes Hanna (IL); David Maimon, Atlit (IL)

(73) Assignee: Edwards Lifesciences Corporation, Irvine, CA (US)

( * ) Notice: Subject to any disclaimer, the term of this patent is extended or adjusted under 35 U.S.C. 154(b) by 555 days.

(21) Appl. No.: 18/131,325

(22) Filed: Apr. 5, 2023

(65) Prior Publication Data

US 2023/0240843 A1 Aug. 3, 2023

Related U.S. Application Data

(63) Continuation of application No. PCT/US2021/053673, filed on Oct. 5, 2021.

(Continued)

(51) Int. Cl.
*A61F 2/24* (2006.01)

(52) U.S. Cl.
CPC .......... *A61F 2/2418* (2013.01); *A61F 2/2403* (2013.01)

(58) Field of Classification Search
CPC .................. A61F 2/2418; A61F 2/2403; A61F 2220/0041; A61F 2220/0091
See application file for complete search history.

(56) References Cited

U.S. PATENT DOCUMENTS

| | | | |
|---|---|---|---|
| 3,409,013 | A | 11/1968 | Berry |
| 3,548,417 | A | 12/1970 | Ronnie et al. |

(Continued)

FOREIGN PATENT DOCUMENTS

| | | |
|---|---|---|
| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in CLosed Chest Pig," European Heart Journal, No. 13. pp. 704-708. 1992.

(Continued)

*Primary Examiner* — Suzette J Gherbi
(74) *Attorney, Agent, or Firm* — Klarquist Sparkman, LLP

(57) ABSTRACT

An implantable prosthetic device can include a radially expandable and compressible frame including an inflow end portion and an outflow end portion. The frame can include an expansion and locking mechanism comprising a member having a first set of lateral extensions disposed adjacent an outflow end and a second set of lateral extensions axially spaced from the first set, each lateral extension comprising a bore extending into the lateral extension. The frame can further comprise a commissure attachment member having a first set of arms each extending into a respective inner bore of the first set of lateral extensions and a second set of arms each extending into a respective inner bore of the second set of lateral extensions such that the commissure attachment member is restrained from movement relative to the expansion and locking mechanism in the radial and axial directions.

17 Claims, 21 Drawing Sheets

Related U.S. Application Data

(60) Provisional application No. 63/234,512, filed on Aug. 18, 2021, provisional application No. 63/088,362, filed on Oct. 6, 2020.

(56) References Cited

U.S. PATENT DOCUMENTS

| | | |
|---|---|---|
| 3,587,115 A | 6/1971 | Donald |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |

(56)     References Cited

U.S. PATENT DOCUMENTS

| | | | |
|---|---|---|---|
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 11,224,509 B2 | 1/2022 | Dasi et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0105153 A1* | 4/2019 | Barash ................. A61F 2/2418 |
| 2019/0159894 A1 | 5/2019 | Levi et al. |
| 2019/0192288 A1 | 6/2019 | Levi et al. |
| 2019/0192289 A1 | 6/2019 | Levi et al. |
| 2022/0154370 A1* | 5/2022 | Han ...................... A61F 2/2463 |
| 2022/0257367 A1* | 8/2022 | Neumann ............... A61F 2/844 |

(56) References Cited

U.S. PATENT DOCUMENTS

| | | | | |
|---|---|---|---|---|
| 2023/0149159 A1* | 5/2023 | Levi | A61F 2/2415 | 623/2.11 |
| 2023/0149165 A1* | 5/2023 | Nir | A61F 2/243 | 623/2.1 |
| 2023/0165676 A1* | 6/2023 | Maimon | A61F 2/24 | 623/2.1 |
| 2023/0285144 A1* | 9/2023 | Yushtein | A61F 2/243 | |
| 2024/0074851 A1* | 3/2024 | Nir | A61F 2/2415 | |
| 2024/0091004 A1* | 3/2024 | Nir | A61F 2/2418 | |
| 2025/0000644 A1* | 1/2025 | Nir | A61F 2/2418 | |
| 2025/0009505 A1* | 1/2025 | Harel | A61F 2/243 | |
| 2026/0007512 A1* | 1/2026 | Bukin | A61F 2/2409 | |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 1991017720 A1 | 11/1991 |
| WO | 1992017118 A1 | 10/1992 |
| WO | 1993001768 A1 | 2/1993 |
| WO | 1997024080 A1 | 7/1997 |
| WO | 1998029057 A1 | 7/1998 |
| WO | 1999030646 A1 | 6/1999 |
| WO | 1999033414 A1 | 7/1999 |
| WO | 1999040964 A1 | 8/1999 |
| WO | 1999047075 A1 | 9/1999 |
| WO | 2000018333 A1 | 4/2000 |
| WO | 2000041652 A1 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001062189 A1 | 8/2001 |
| WO | 2001064137 A1 | 9/2001 |
| WO | 2001076510 A2 | 10/2001 |
| WO | 2002022054 A1 | 3/2002 |
| WO | 2002036048 A1 | 5/2002 |
| WO | 2002041789 A2 | 5/2002 |
| WO | 2002043620 A1 | 6/2002 |
| WO | 2002047575 A2 | 6/2002 |
| WO | 2002049540 A2 | 6/2002 |
| WO | 2003047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

\* cited by examiner

COMMISSURE LOCKING MEMBER

CROSS-REFERENCE TO RELATED APPLICATIONS

This application is a continuation of International Application No. PCT/US2021/053673, filed Oct. 5, 2021, which claims the benefit of U.S. Provisional Application No. 63/234,512, filed Aug. 18, 2021, and U.S. Provisional Application No. 63/088,362, filed Oct. 6, 2020, all of which are incorporated by reference herein in their entirety.

FIELD

The present disclosure related to prosthetic heart valves, and to methods and assemblies for attaching a valvular structure to a frame of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size. Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. Typically, the leaflets are attached to an inner surface of the frame of the prosthetic valve. However, actuators or other internal components of the frame can interfere with leaflet attachment.

Accordingly, there remains a need for improved transcatheter heart valves and leaflet attachment configurations for such valves.

SUMMARY

In a representative example, an implantable prosthetic device can comprise a radially expandable and compressible frame, the frame comprising an inflow end portion and an outflow end portion, and expansion and locking mechanism, and a commissure attachment member. The expansion and locking mechanism can comprise a member coupled to the frame at a first location, the member comprising a first set of lateral extensions disposed adjacent an outflow end of the first member and a second set of lateral extensions axially spaced from the first set, each lateral extension comprising a bore extending into the lateral extension. The commissure attachment member can have a first set of arms each extending into a respective inner bore of a lateral extension of the first set of lateral extensions and a second set of arms each extending into a respective inner bore of a lateral extension of the second set of lateral extensions such that the commissure attachment member is restrained from movement relative to the expansion and locking mechanism in the radial and axial directions. Each commissure attachment member can be configured to couple a portion a valvular structure to a respective expansion and locking mechanism.

In a representative example, a method of assembling a prosthetic valve can comprise coupling adjacent tabs of adjacent leaflets of a valvular structure to a commissure attachment member, the commissure attachment member comprising a first set of arms and a second set of arms axially spaced from the first set of arms, each arm comprising a laterally extending portion and an axially extending portion, and aligning the commissure attachment member over an expansion and locking mechanism of a prosthetic valve such that the first set of arms are aligned with respective inner bores of a first set of lateral extensions extending laterally from the expansion and locking mechanism and such that the second set of arms are aligned with respective inner bores of a second set of lateral extensions extending laterally from the expansion and locking mechanism, the second set of lateral extensions being axially spaced from the first set of lateral extensions. The method can further comprise inserting the axially extending portions of the first set of arms into the respective inner bores of the first set of lateral extensions and the axially extending portions of the second set of arms into the respective inner bores of the second set of lateral extensions, such that the commissure attachment member is restrained from movement relative to the expansion and locking mechanism in the radial and axial directions.

In a representative example, an implantable prosthetic device can comprise a radially expandable and compressible frame, the frame comprising an inflow end portion, an outflow end portion, and a commissure post comprising a first set of lateral extensions disposed adjacent an outflow end of the commissure post and a second set of lateral extensions spaced apart from the first set, each lateral extension comprising an inner bore. The device can further comprise a commissure attachment member having a first set of arms each extending into a respective inner bore of a lateral extension of the first set of lateral extensions and a second set of arms each extending into a respective inner bore of a lateral extension of the second set of lateral extensions such that the commissure attachment member is restrained from movement relative to the commissure post in the radial and axial directions. Each commissure attachment member can be configured to couple a portion a valvular structure to a respective commissure post.

In another representative example, an implantable prosthetic device can comprise a radially expandable and compressible frame, the frame comprising an inflow end portion and an outflow end portion, and an expansion and locking mechanism comprising a first member coupled to the frame at a first location, the member comprising one or more lateral extensions disposed adjacent an outflow end of the first member and one or more projections extending from a side wall of the expansion and locking mechanism and axially spaced from the lateral extensions, each lateral extension comprising a bore extending into the lateral extension. The prosthetic device can further comprise a commissure attachment member having one or more first arms each extending into a respective inner bore of a lateral extension and one or more second arms each configured to engage a respective projection such that such that the commissure attachment member is restrained from movement relative to the expansion and locking mechanism in the radial and axial directions, each first and second arm comprising a laterally extending portion and an axially extending portion coupled to the laterally extending portion. Each commissure attachment member can be configured to couple a portion a valvular structure to a respective expansion and locking mechanism.

In a representative example, a method of assembling a prosthetic valve can comprise coupling adjacent tabs of adjacent leaflets of a valvular structure to a commissure attachment member, the commissure attachment member comprising a first set of arms and a second set of arms axially spaced from the first set of arms, each arm comprising a laterally extending portion and an axially extending portion, and aligning the commissure attachment member over an expansion and locking mechanism of a prosthetic valve such that the first set of arms are axially aligned with respective inner bores of a set of lateral extensions extending laterally from the expansion and locking mechanism and such that the second set of arms are laterally aligned with respective projections extending laterally from the expansion and locking mechanism, the projections being axially spaced from the set of lateral extensions and each comprising an angled surface. The method can further comprise inserting the axially extending portions of the first set of arms into the respective inner bores of the set of lateral extensions, thereby restraining an outflow end portion of the commissure attachment member from radial movement relative to the expansion and locking mechanism, and applying a force to an inflow end portion of the commissure attachment member such the second set of arms engages the projections, thereby restraining the inflow end portion of the commissure attachment member from radial movement relative to the expansion and locking mechanism.

In another representative example, an implantable prosthetic device can comprise a radially expandable and compressible frame, the frame comprising an inflow end portion and an outflow end portion, and an expansion and locking mechanism comprising a first member coupled to the frame at a first location, the member comprising a first set of lateral extensions disposed adjacent an outflow end of the first member and one or more projections extending from a side wall of the expansion and locking mechanism and axially spaced from the lateral extensions, each lateral extension comprising a bore extending into the lateral extension. The device can further comprise a commissure attachment member having one or more of first arms each extending into a respective inner bore of a lateral extension of the first set of lateral extensions and one or more second arms each configured to engage a respective projection of the one or more projections such that such that the commissure attachment member is retained from movement relative to the expansion and locking mechanism in the axial direction, each first and second arm comprising a laterally extending portion, the first arms further comprising an axially extending portion coupled to the laterally extending portion. The commissure attachment member can be configured to couple a portion a valvular structure to a respective expansion and locking mechanism.

In still another representative example, an implantable prosthetic device can comprise a radially expandable and compressible frame, the frame comprising an inflow end portion and an outflow end portion and an expansion and locking mechanism comprising a member coupled to the frame at a first location, the member comprising first and second lateral extensions disposed adjacent an outflow end of the first member and an engagement feature spaced apart from the first and second lateral extensions, each lateral extension comprising a bore extending into the lateral extension. The device can further comprise a commissure attachment member having a first and second arms each extending into a respective inner bore of the first and second lateral extensions and a lower extension extending toward the inflow end portion of the frame and comprising a corresponding engagement feature coupled to the engagement feature of the expansion and locking mechanism. The commissure attachment member can be configured to couple a portion a valvular structure to a respective expansion and locking mechanism.

In a representative example, a method of assembling a prosthetic valve can comprise coupling adjacent tabs of adjacent leaflets of a valvular structure to a commissure attachment member, the commissure attachment member comprising a first and second arms, each arm comprising a laterally extending portion and an axially extending portion, and a lower extension comprising an engagement feature, and aligning the commissure attachment member over an expansion and locking mechanism of a prosthetic valve such that the first and second arms are axially aligned with respective inner bores of first and second lateral extensions extending laterally from the expansion and locking mechanism and such that the engagement feature is aligned with a corresponding engagement feature on a radially inner surface of the expansion and locking mechanism. The method can further comprise inserting the axially extending portions of the first and second arms into the respective inner bores of the first and second lateral extensions, thereby restraining an outflow end portion of the commissure attachment member from radial movement relative to the expansion and locking mechanism, and applying a force to an inflow end portion of the commissure attachment member such the engagement feature engages the corresponding engagement feature of the expansion and locking mechanism, thereby restraining the inflow end portion of the commissure attachment member from movement relative to the expansion and locking mechanism.

The foregoing and other objects, features, and advantages of the disclosure will become more apparent from the following detailed description, which proceeds with reference to the accompanying figures.

5

Figures 6, 7:
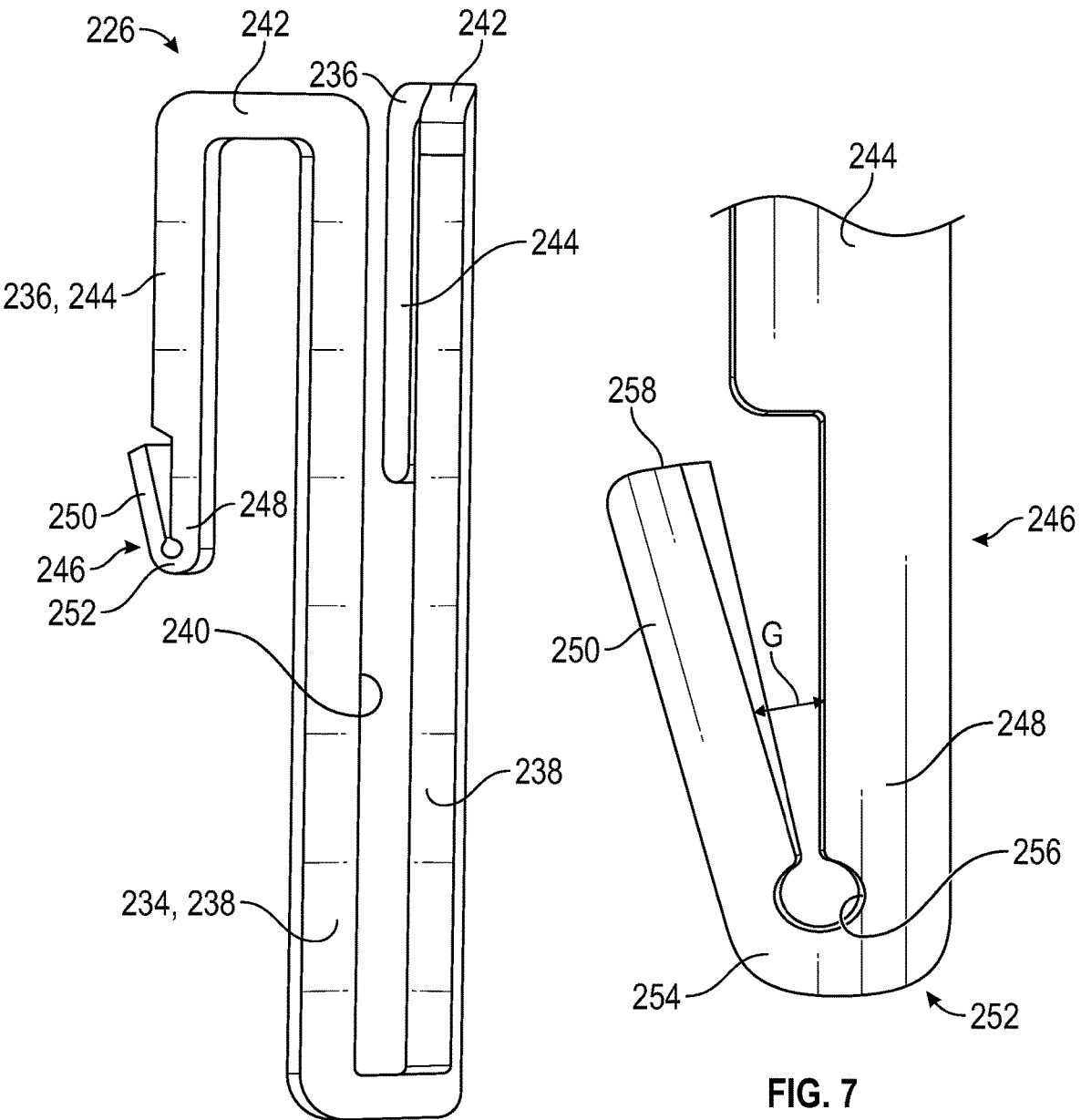
FIG. 6 is a perspective view of a commissure attachment member, according to one example.

FIG. 7 is a side elevation view of a portion of the commissure attachment member of FIG. 6.

Figures 8, 9A, 9B:
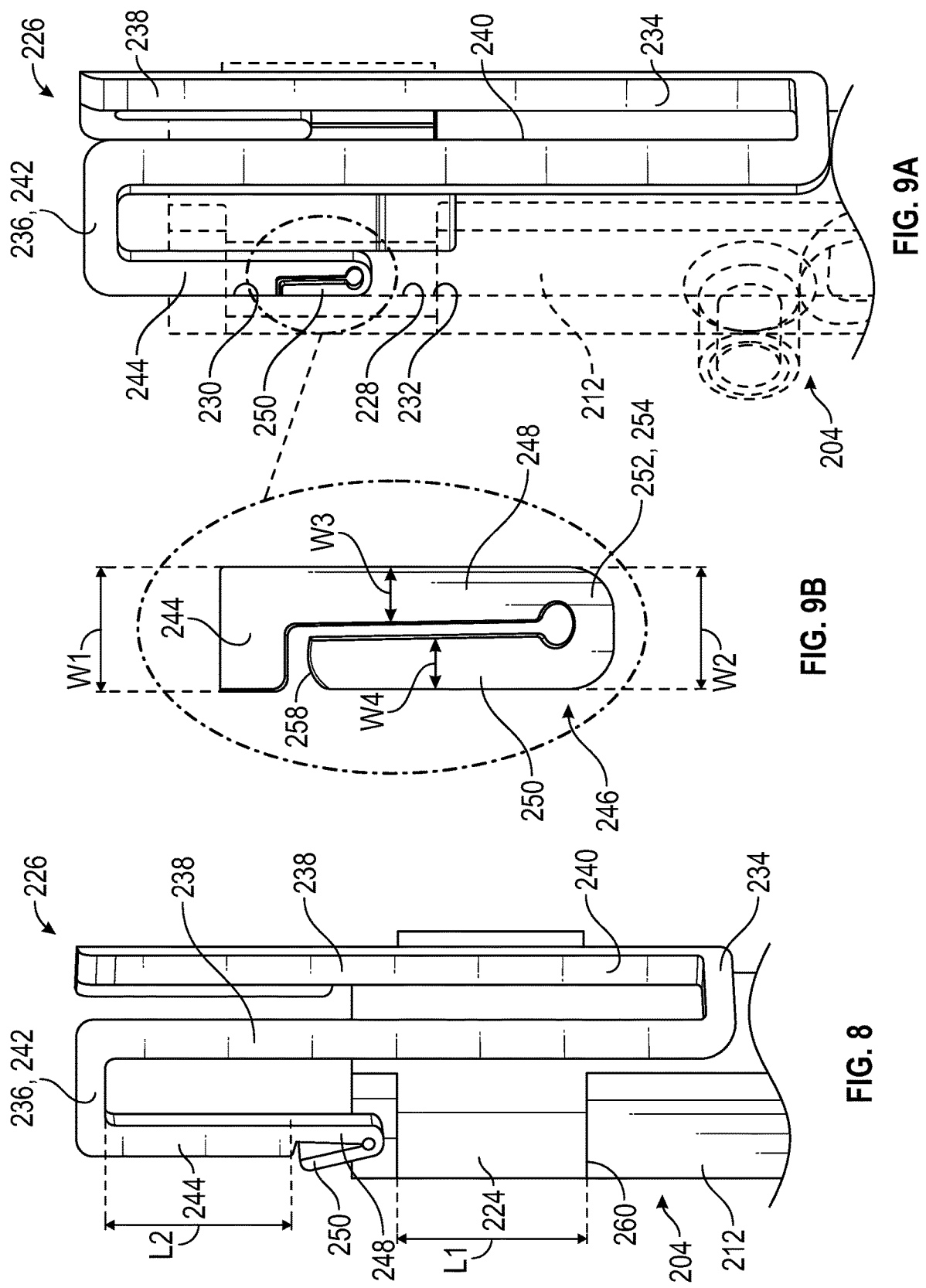

FIG. 8 is a perspective view of the commissure attachment member of FIG. 6 and a portion of an exemplary expansion and locking mechanism.

FIG. 9A is a perspective view of the commissure attachment member of FIG. 6 partially inserted into an expansion and locking mechanism.

FIG. 9B is an enlarged side elevation view of a portion of the commissure attachment member of FIG. 6 shown in the compressed position.

Figures 10, 11:
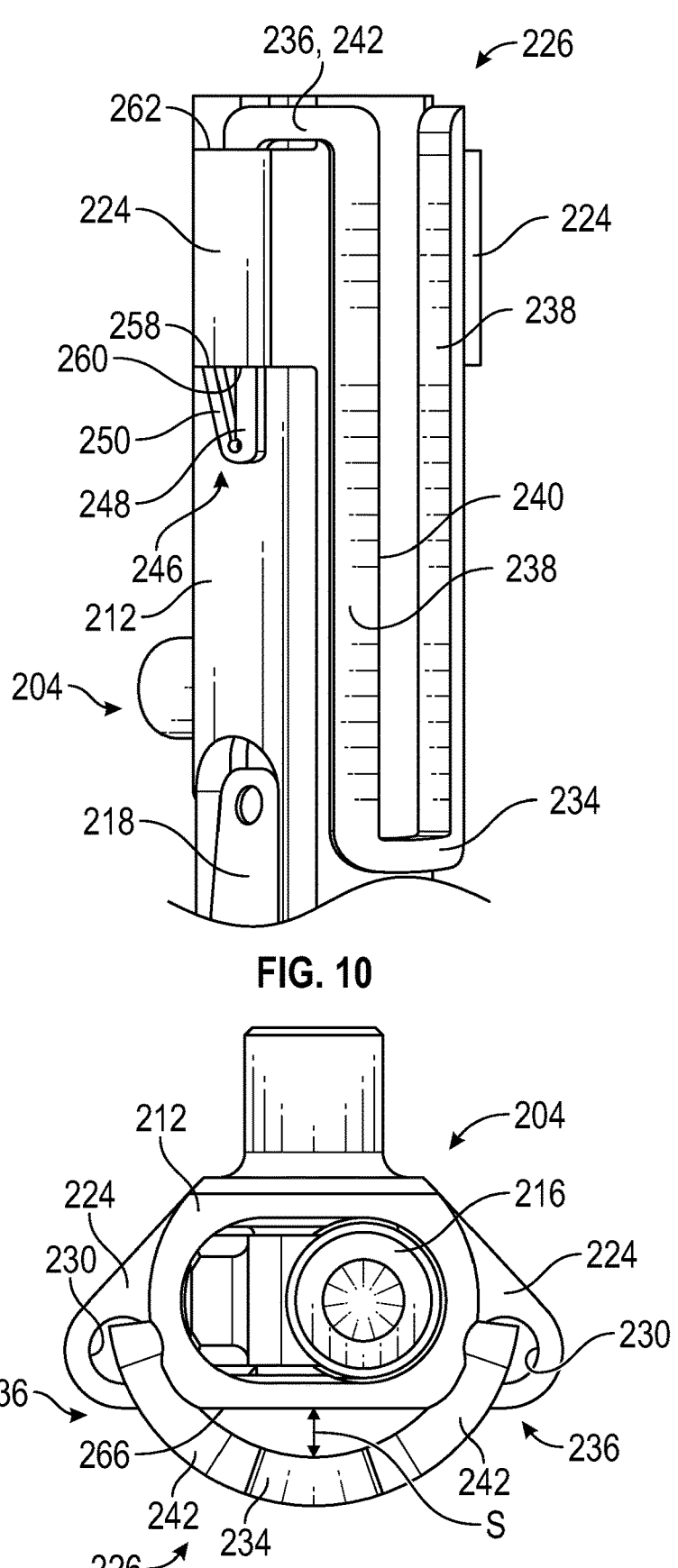

FIG. 10 is a perspective view of the commissure attachment member of FIG. 6 coupled to an expansion and locking mechanism.

FIG. 11 is a top plan view of the commissure attachment member of FIG. 6 coupled to an expansion and locking mechanism.

Figure 12:
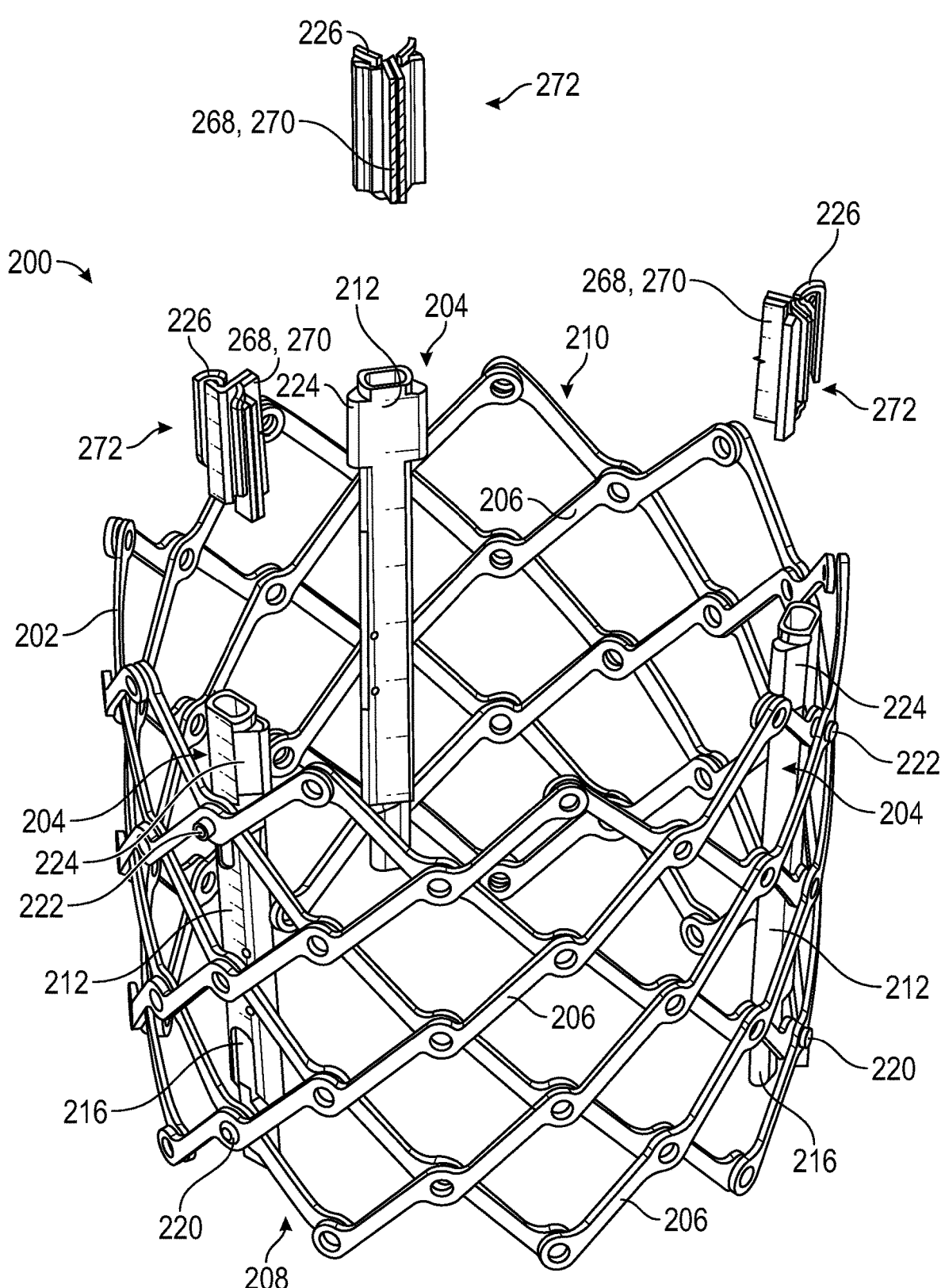

FIG. 12 is a perspective view of a frame for a prosthetic heart valve comprising three expansion and locking mechanisms and three commissure attachment members, according to one example.

Figure 13:
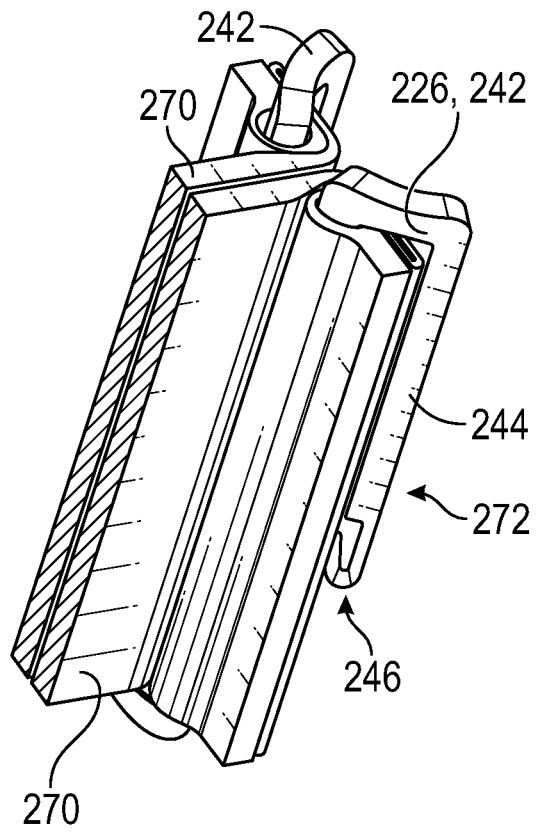

FIG. 13 is a perspective view of the commissure attachment member of FIG. 12 coupled to a portion of a valvular structure.

Figure 14:
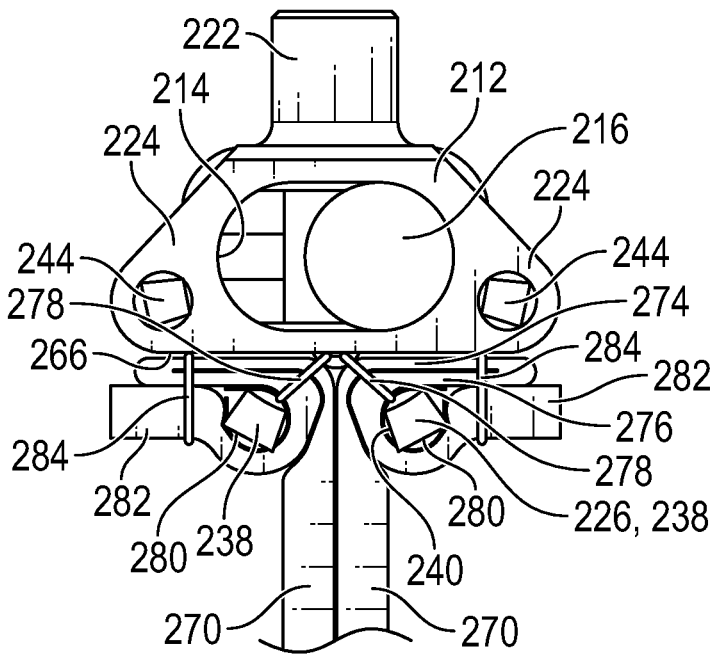

FIG. 14 is a cross-sectional view of an expansion and locking mechanism of FIG. 12 including a commissure assembly.

Figure 15:
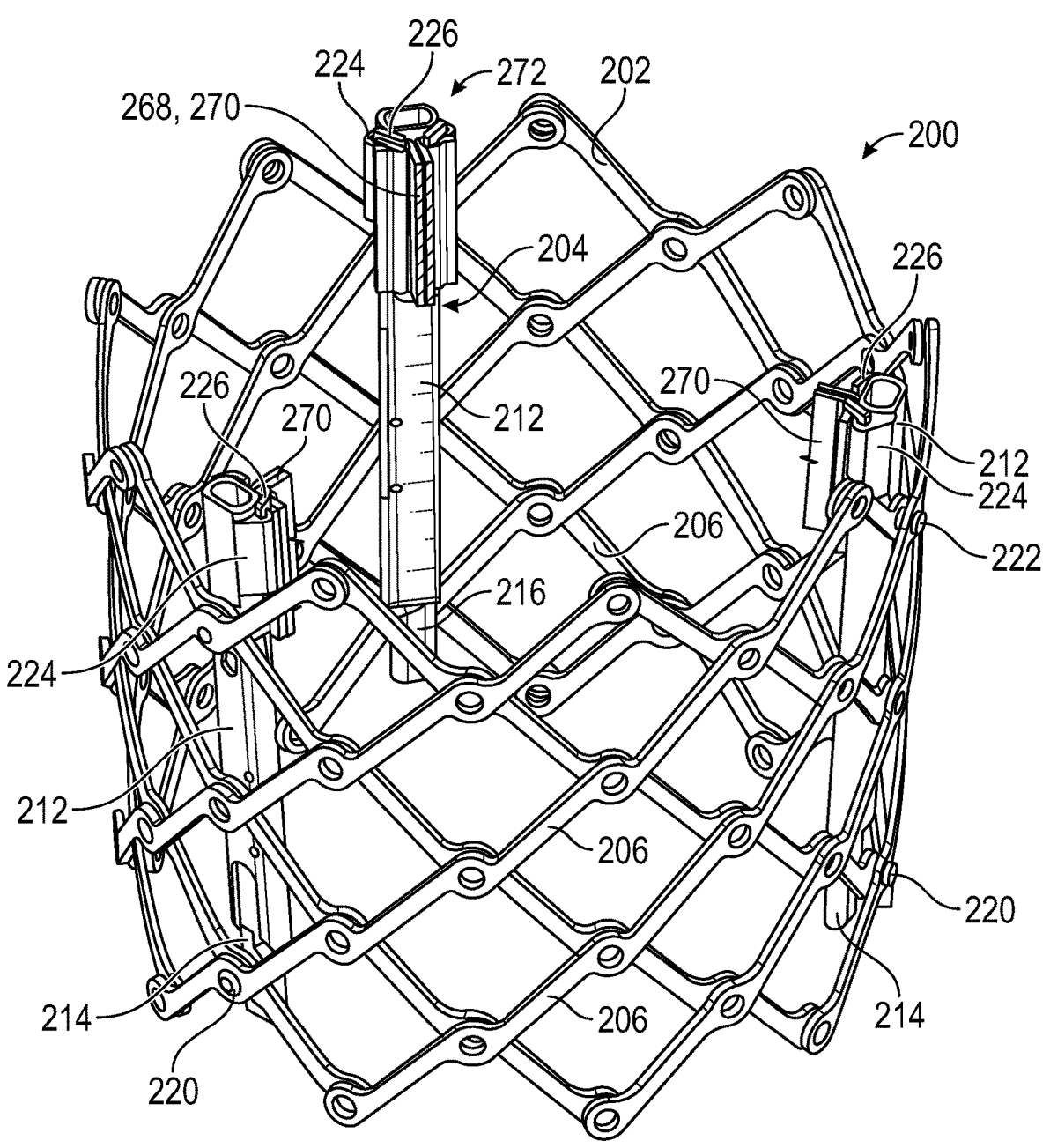

FIG. 15 is a perspective view of the frame of FIG. 12 including three commissure assemblies.

Figure 16:
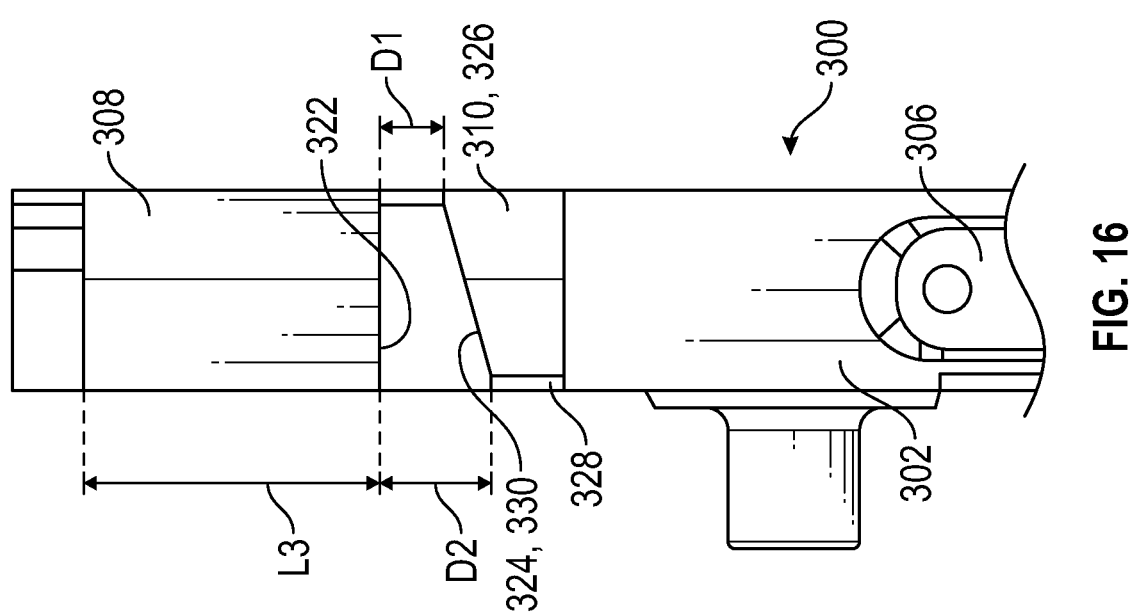

FIG. 16 is a side elevation view of a portion of an expansion and locking mechanism, according to one example.

Figure 17:
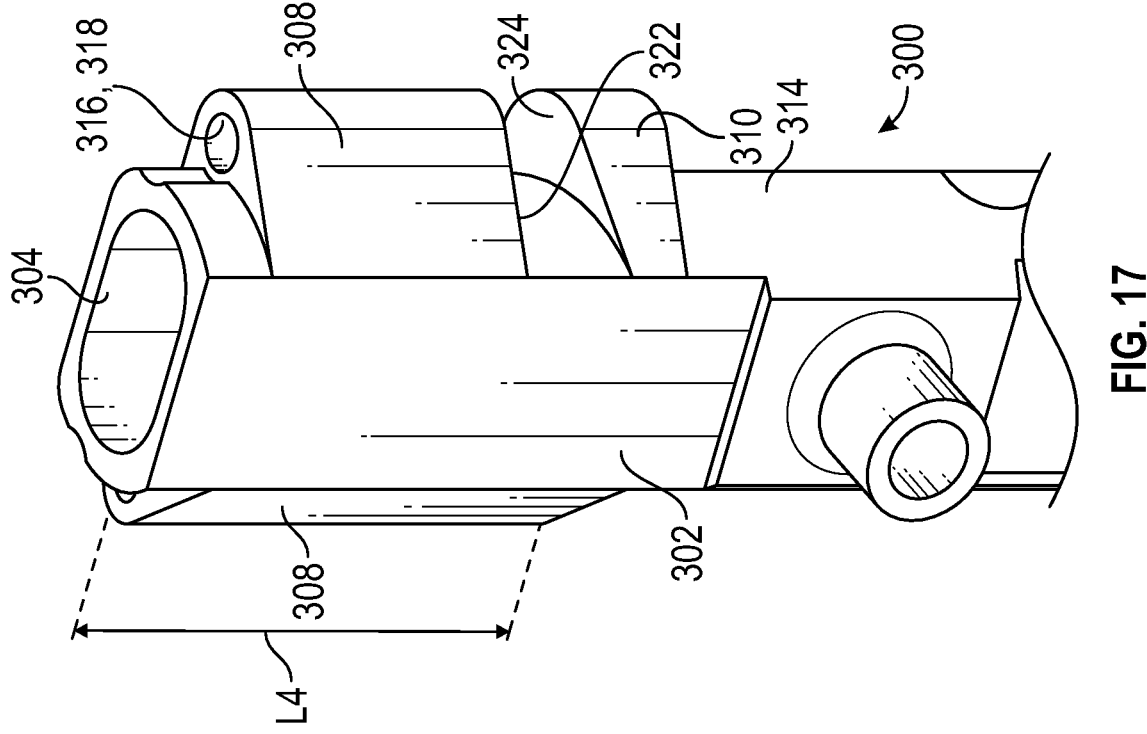

FIG. 17 is a perspective view of a portion of the expansion and locking mechanism of FIG. 16.

Figure 18:
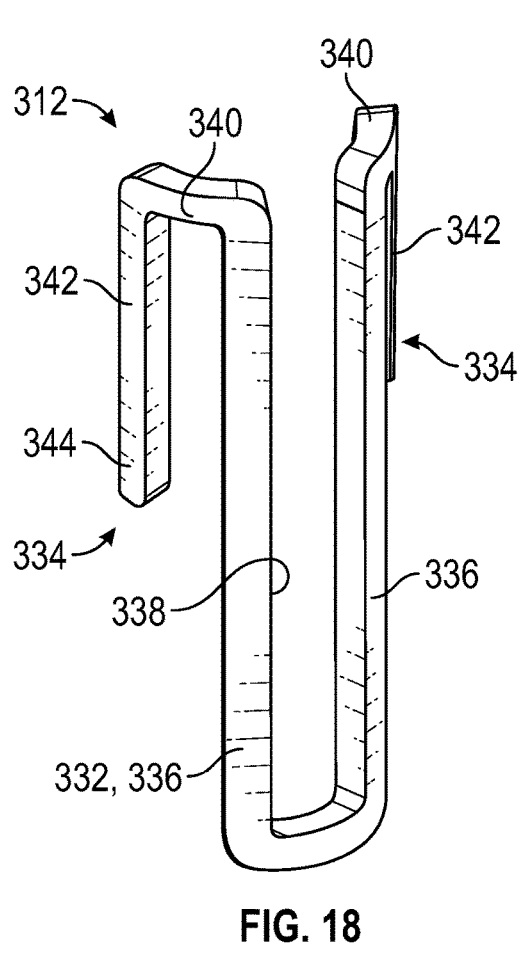

FIG. 18 is a perspective view of a commissure attachment member, according to one example.

Figure 19:
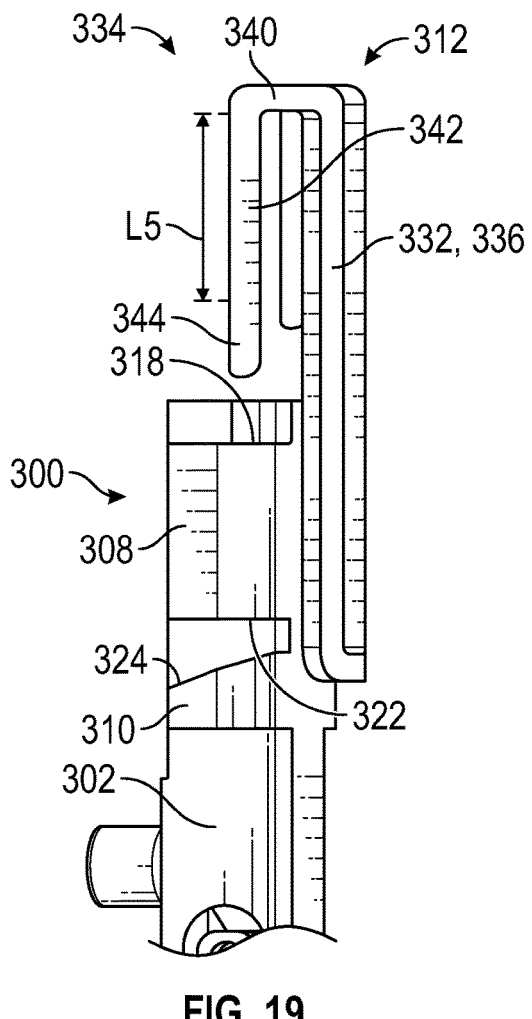

FIG. 19 is a perspective view of the commissure attachment member of FIG. 18 being coupled to the expansion and locking mechanism of FIG. 16.

Figure 20:
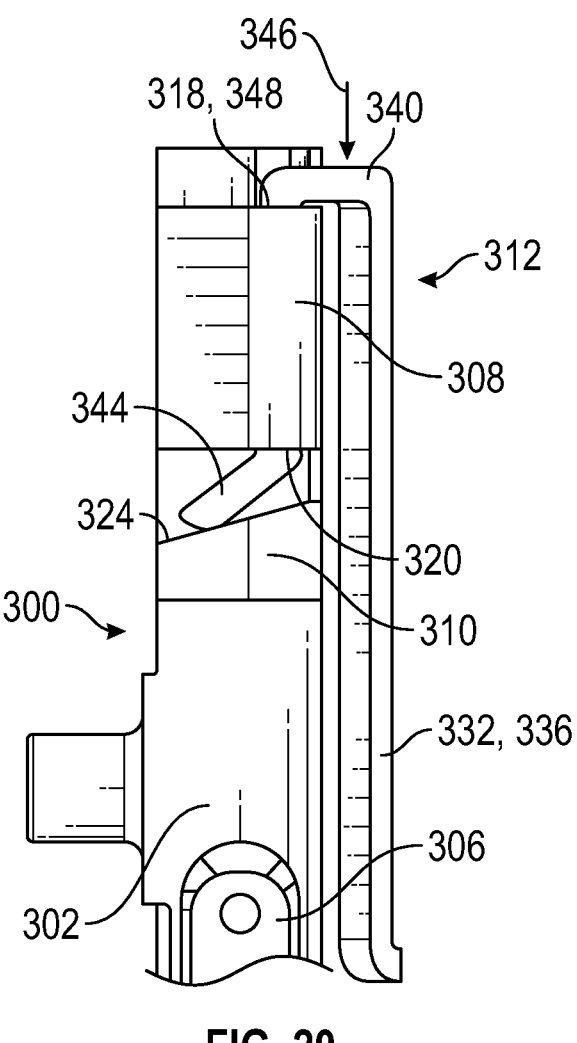

FIG. 20 is a side elevation view of the commissure attachment member of FIG. 18 coupled to the expansion and locking mechanism of FIG. 16.

Figure 21:
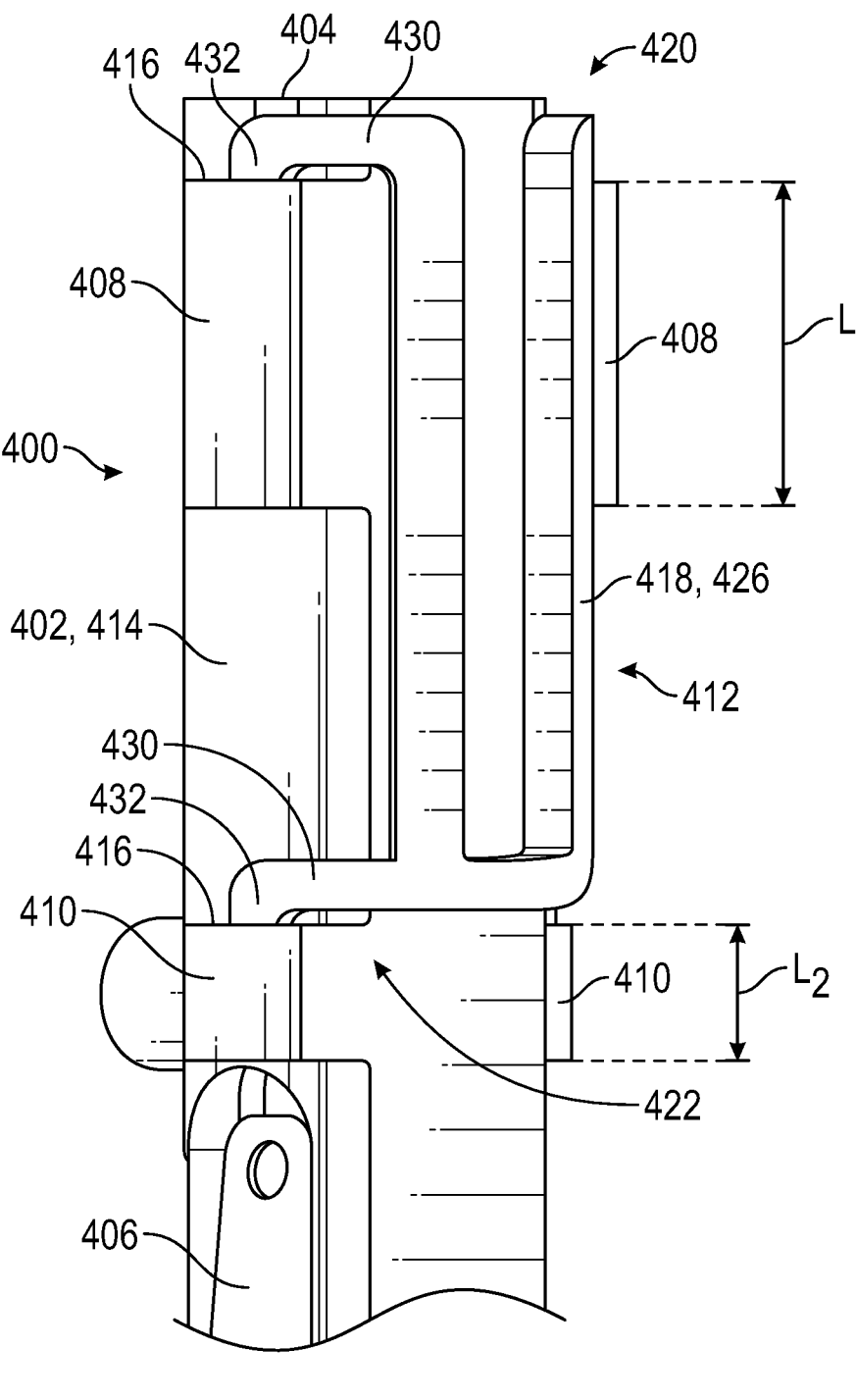

FIG. 21 is a perspective view of a commissure attachment member coupled to an expansion and locking mechanism, according to one example.

Figure 22:
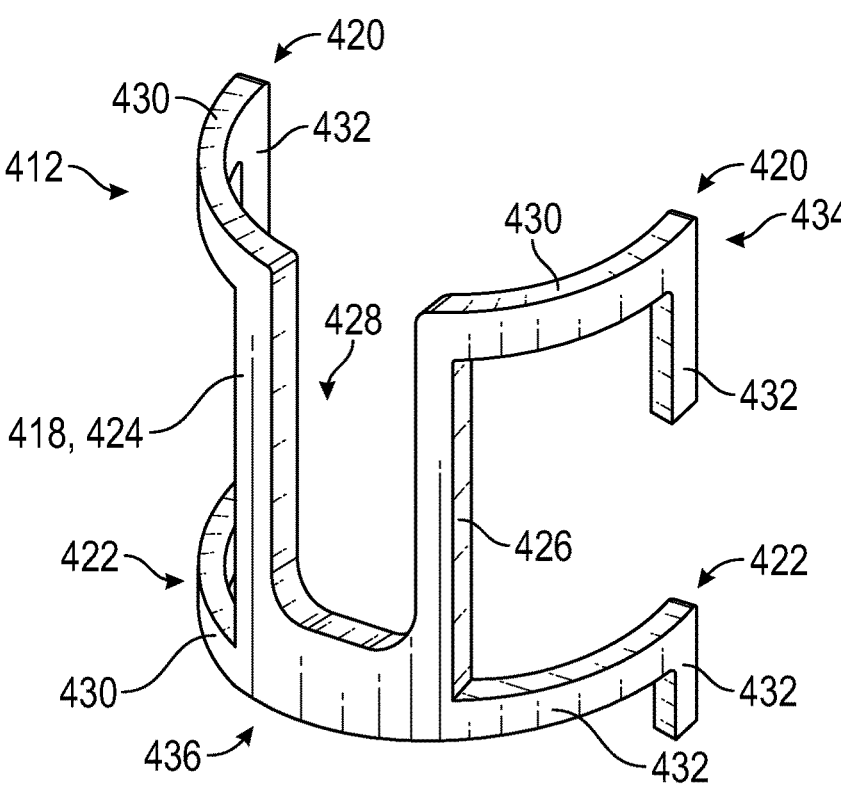

FIG. 22 is a perspective view of the commissure attachment member of FIG. 21.

Figure 23:
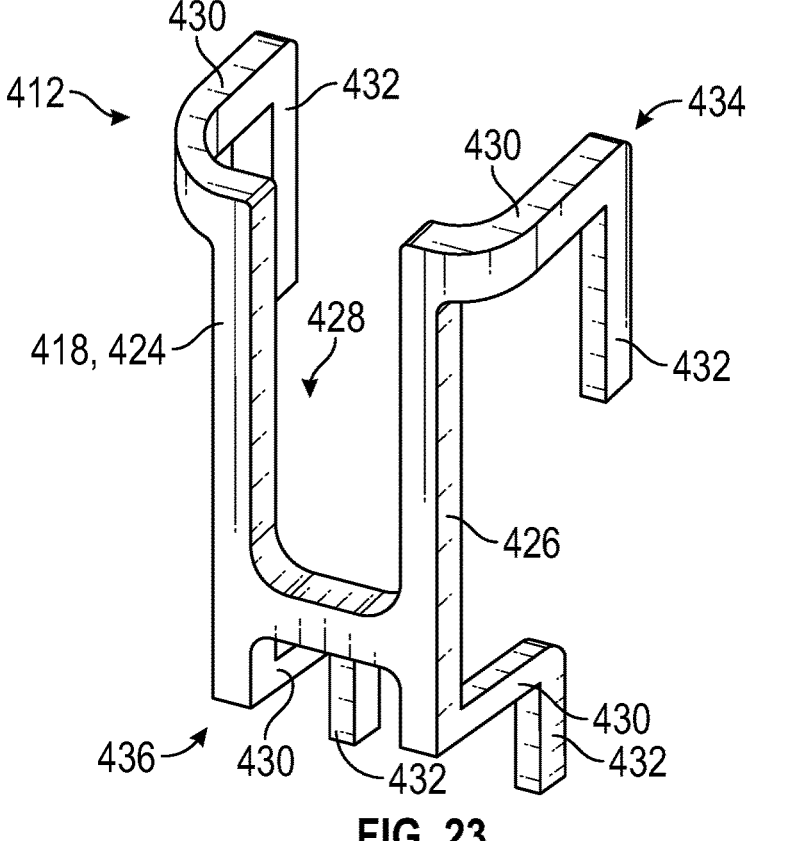

FIG. 23 is a perspective view of a commissure attachment member, according to another example.

Figure 24:
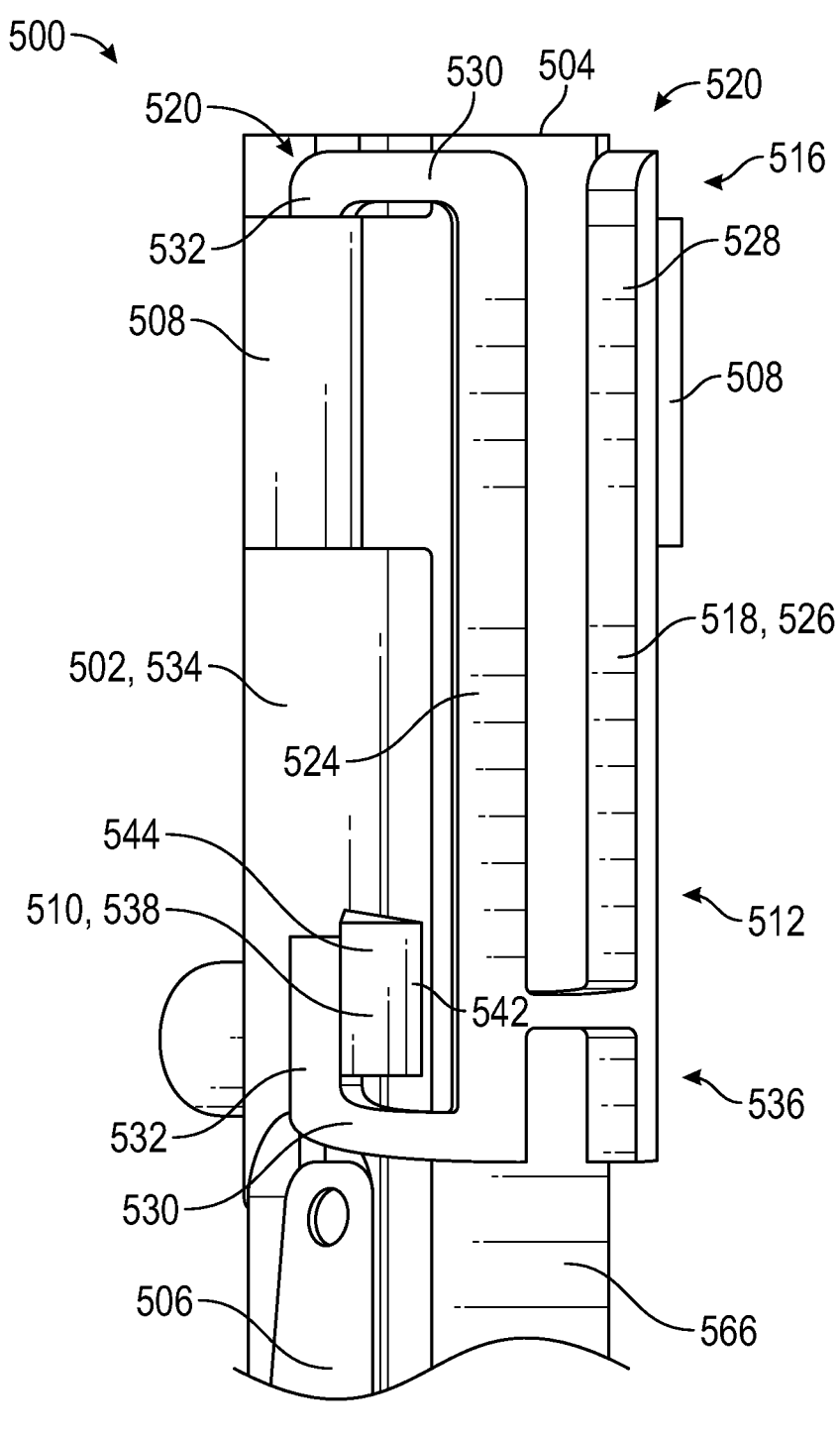

FIG. 24 is a perspective view of a commissure attachment member coupled to an expansion and locking mechanism, according to another example.

Figure 25:
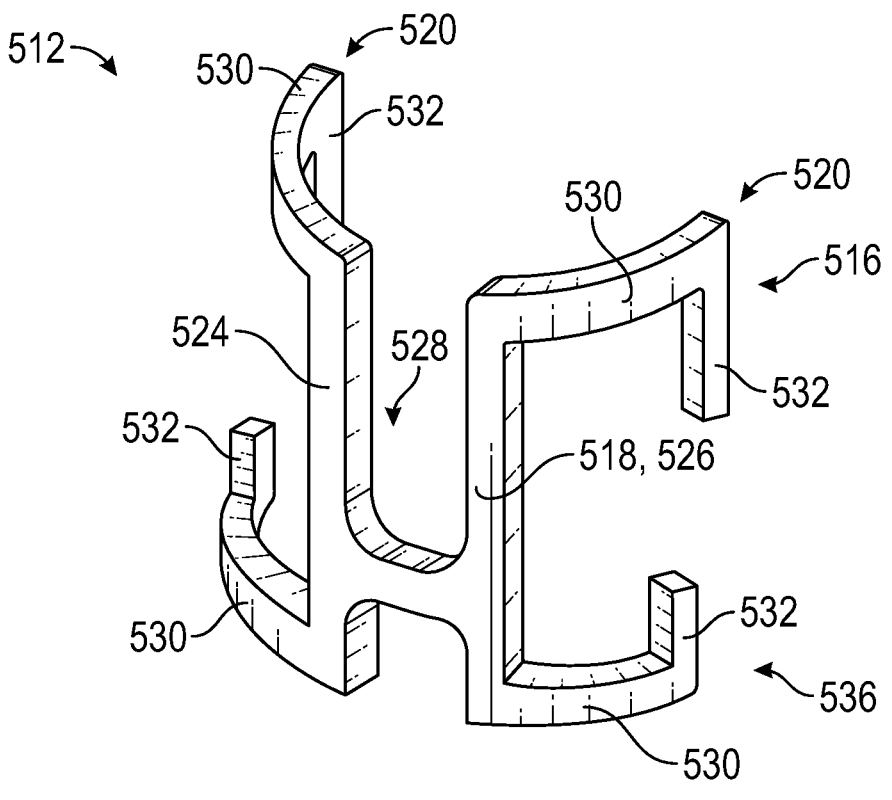

FIG. 25 is a perspective view of the commissure attachment member of FIG. 24.

Figure 26:
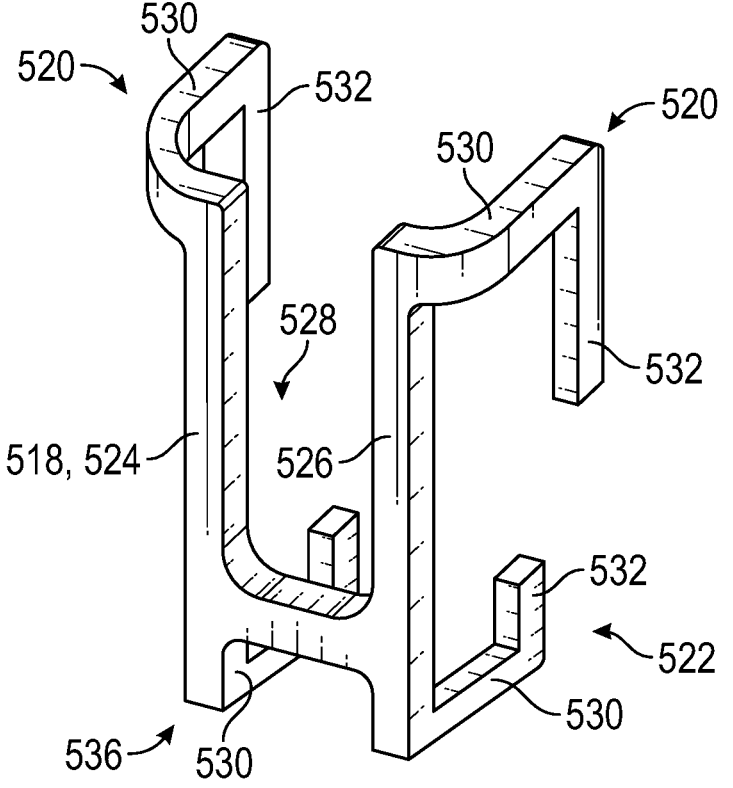

FIG. 26 is a perspective view of a commissure attachment member, according to another example.

Figures 27A, 27B, 27C:
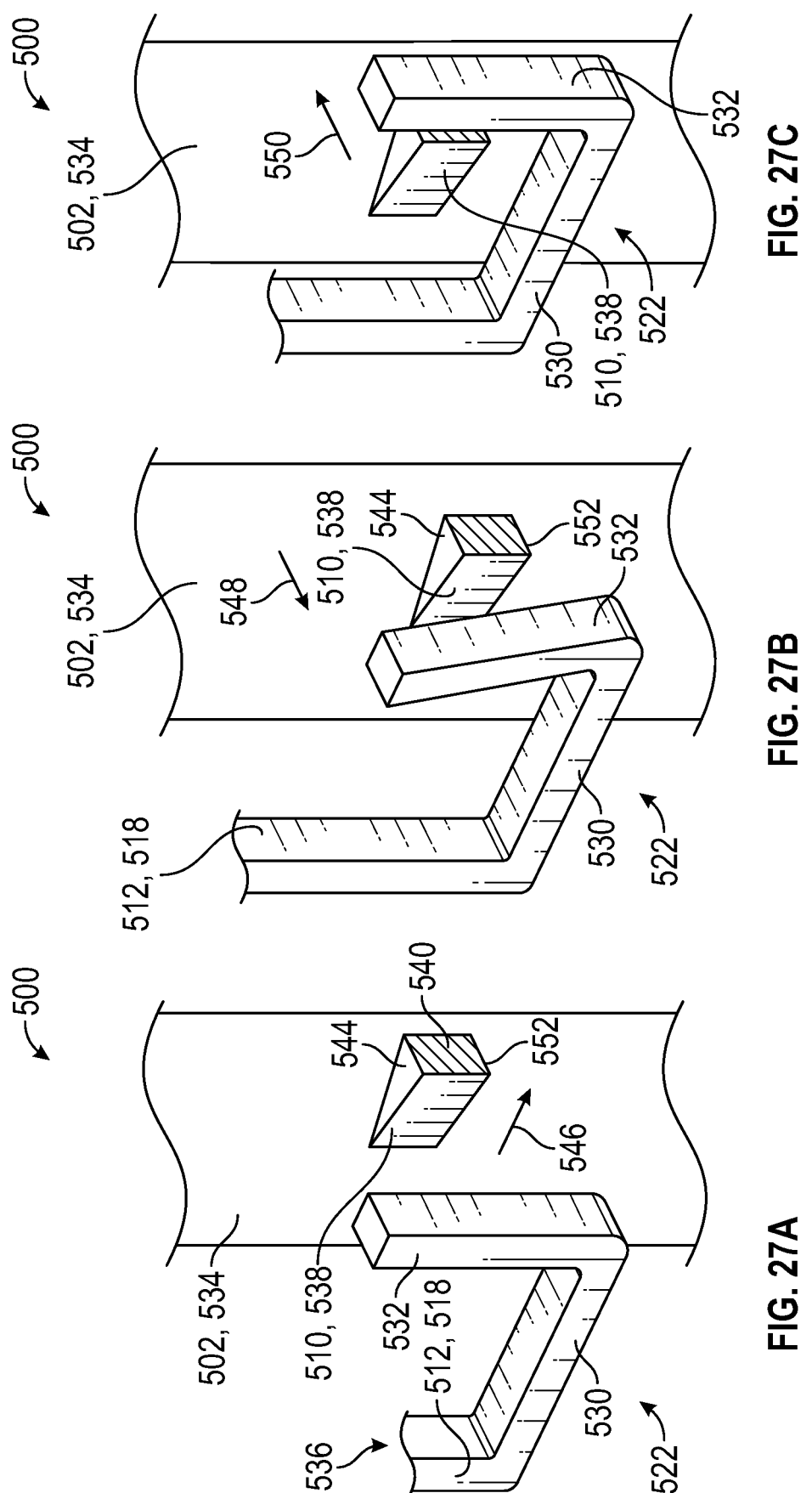

FIGS. 27A-27C are perspective view showing a lower portion of the commissure attachment member of FIG. 26 being coupled to an expansion and locking mechanism.

Figure 28:
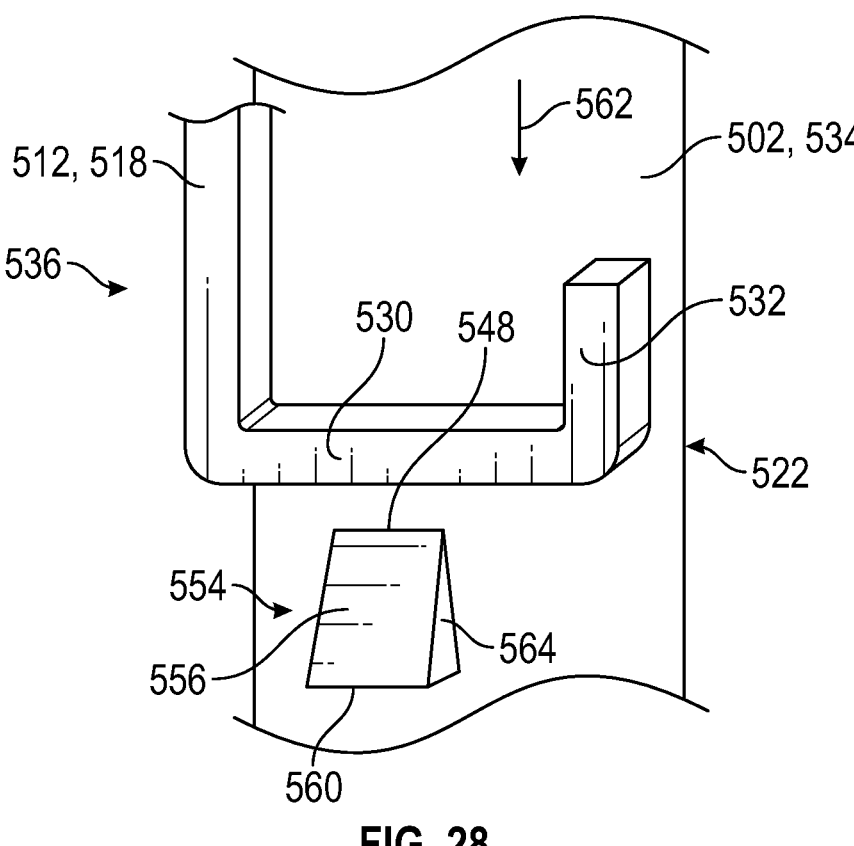

FIG. 28 is a side elevational view of a portion of a commissure attachment member being coupled to an expansion and locking mechanism, according to one example.

Figure 29:
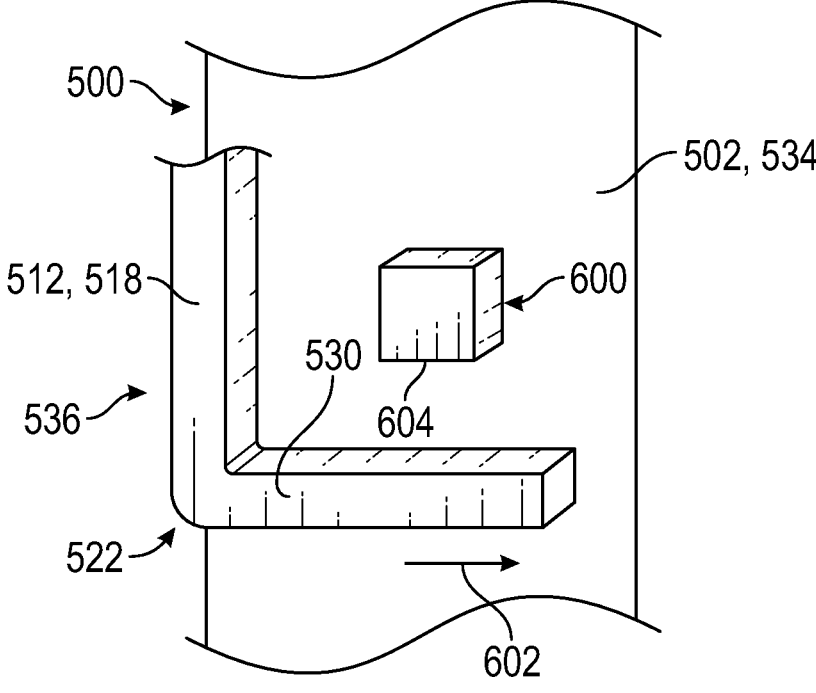

FIG. 29 is a side elevational view of a portion of a commissure attachment member being coupled to an expansion and locking mechanism, according to another example.

Figure 30:
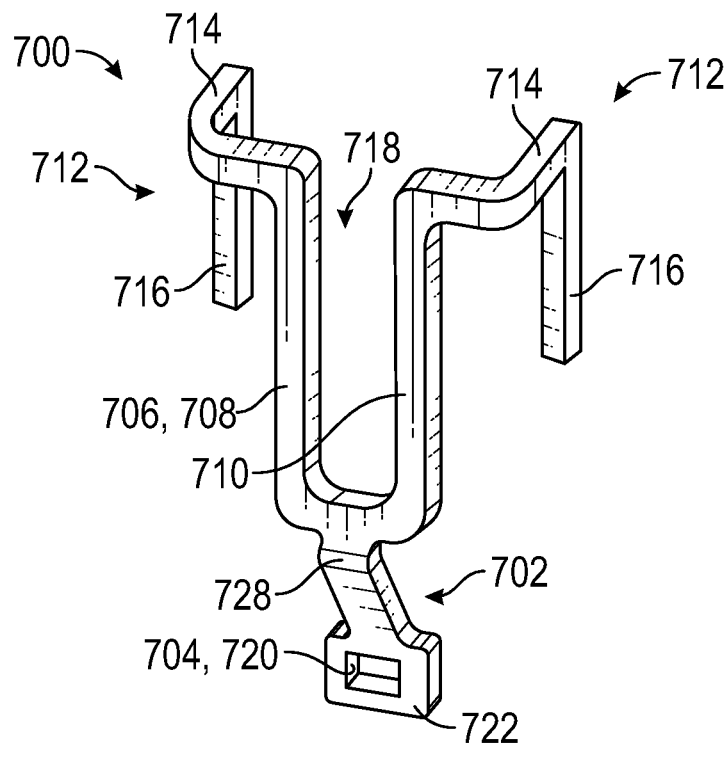
Figure 31:
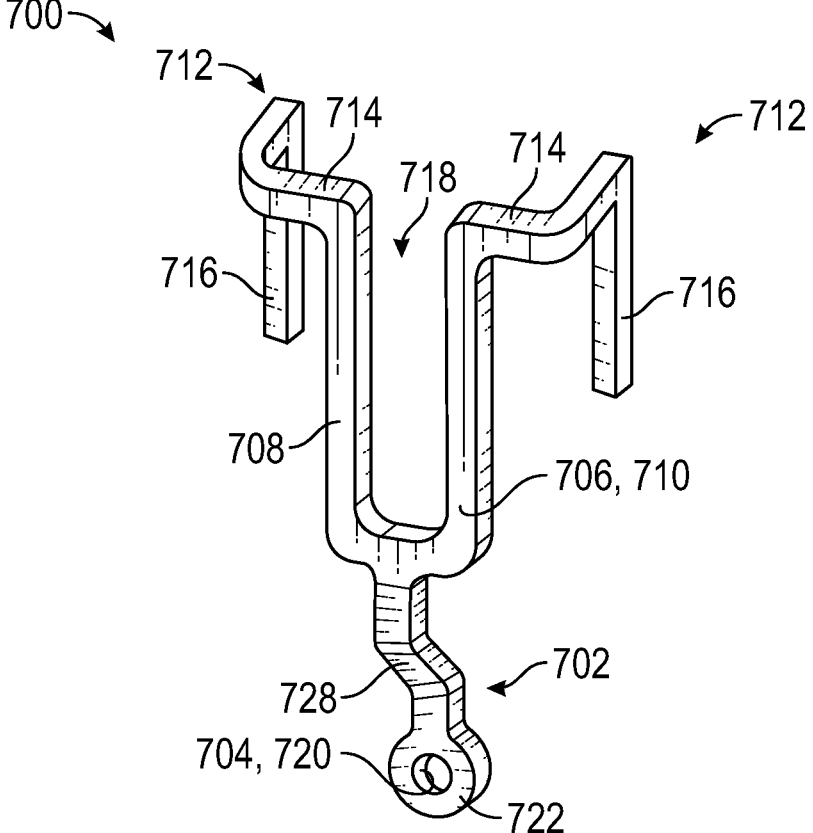
Figure 32:
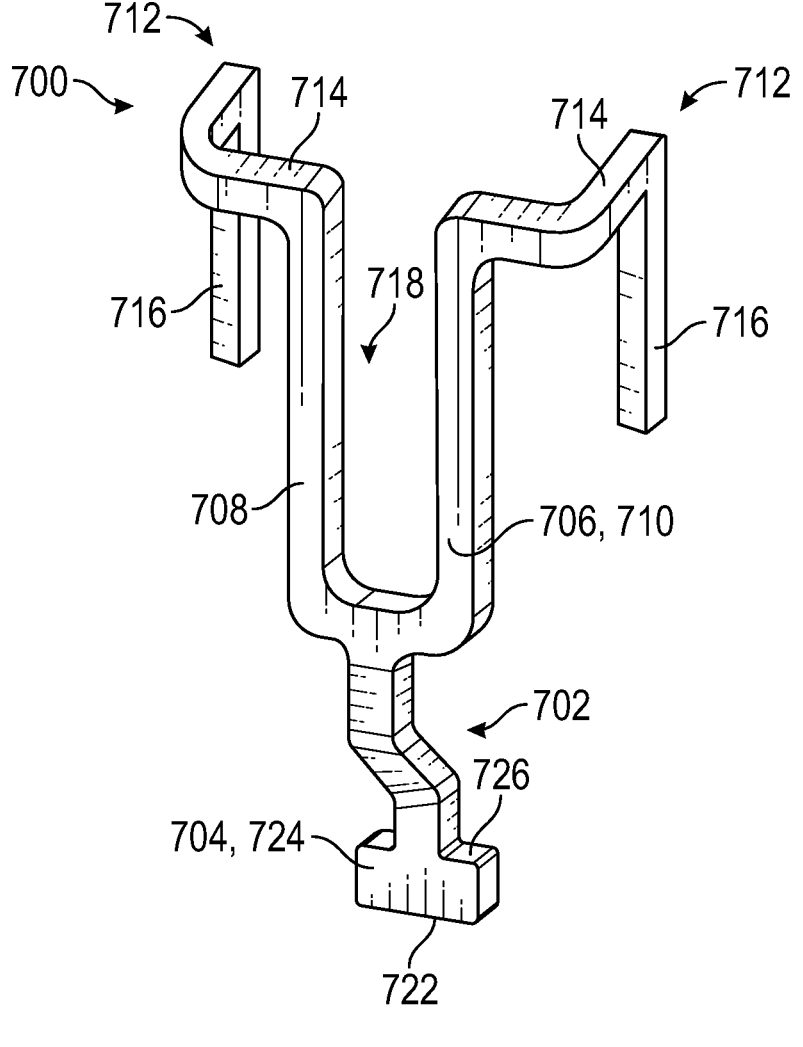

FIGS. 30-32 are perspective views of various examples of a commissure attachment member.

6

DETAILED DESCRIPTION

General Considerations

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

Figure 2:
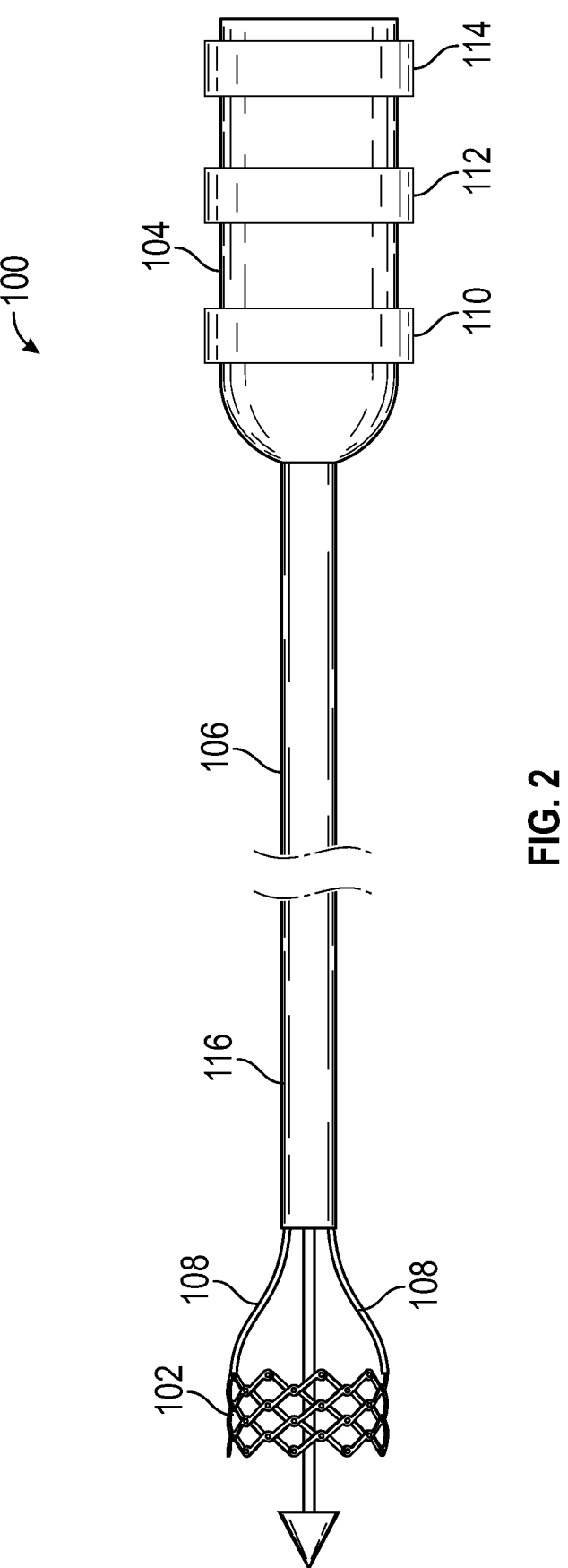
FIG. 2 is a side elevation view of a delivery apparatus for a prosthetic heart valve, according to one example.
Figure 3:
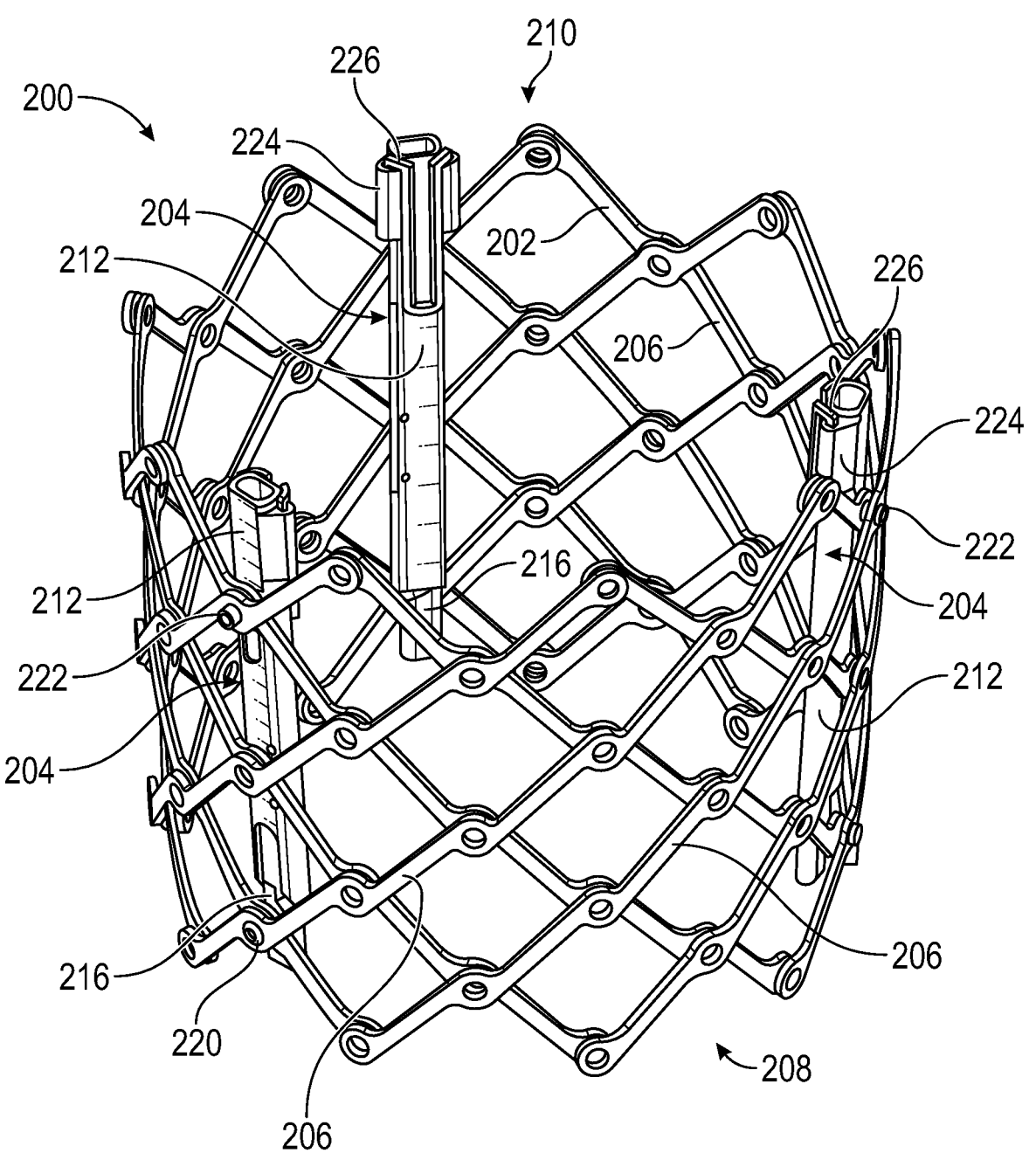
FIG. 3 is a perspective view of a prosthetic heart valve, according to another example.

All features described herein are independent of one another and, except where structurally impossible, can be used in combination with any other feature described herein. For example, a delivery apparatus 100 as shown in FIG. 2 can be used in combination with prosthetic valve 200 described herein. In another example, expansion and locking mechanisms 204 or 300 as shown in FIG. 3 and FIG. 16 can be used in combination with the prosthetic valve 10 shown in FIG. 1.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Examples of the Disclosed Technology

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the valves disclosed herein may be used with a variety of implant delivery apparatuses, and examples thereof will be discussed in more detail later.

Figure 1:
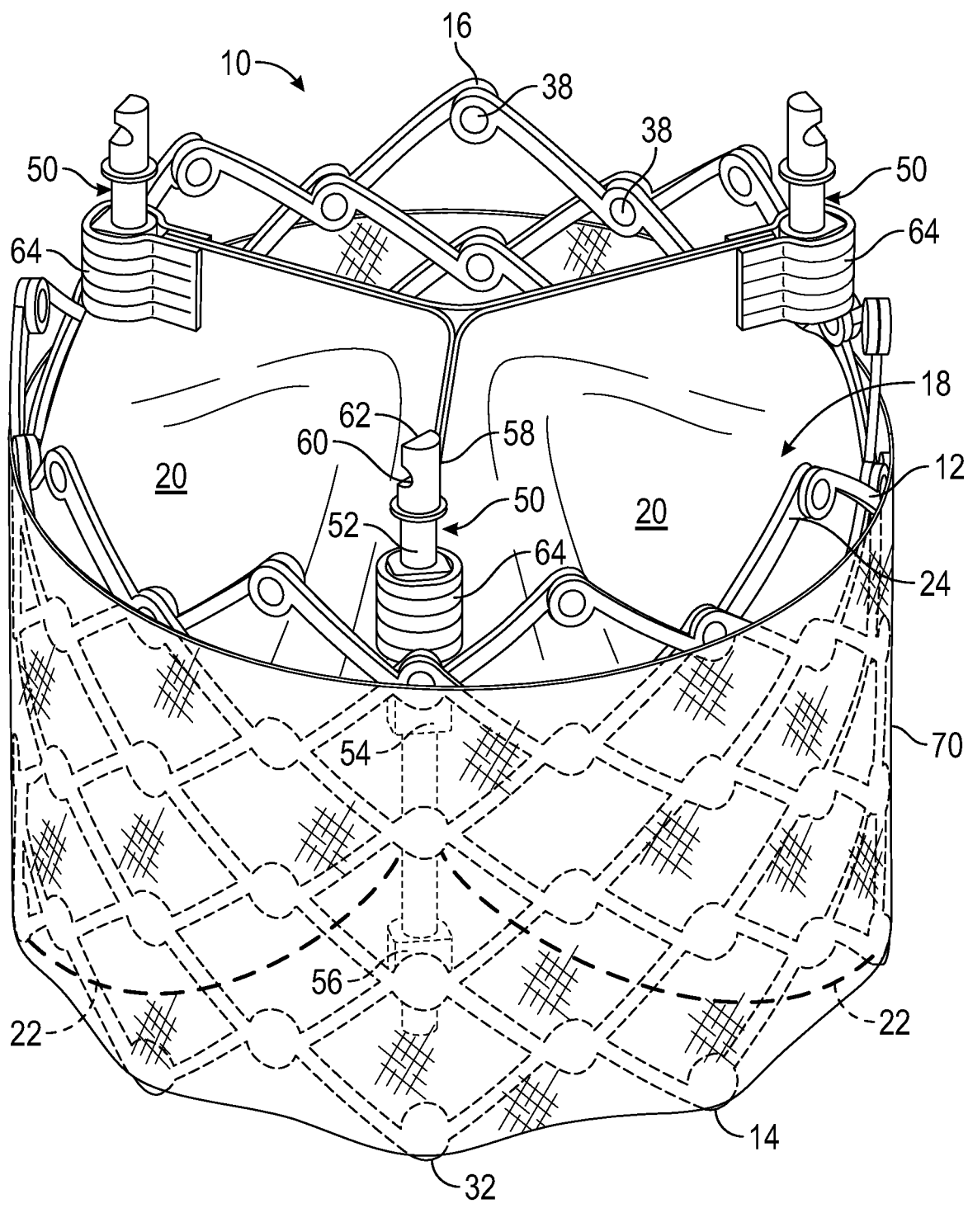
FIG. 1 is a perspective view of a prosthetic heart valve, according to one example.

FIG. 1 shows an exemplary prosthetic valve 10, according to one example. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator 50 or the frame 12.

In the depicted example, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some examples, the inflow edge portions 22 of the leaflets 20 can be sutured to adjacent struts of the frame generally along the scallop line. In other examples, the inflow edge portions 22 of the leaflets 20 can be sutured to an inner skirt, which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, 8,252,202, and 11,135,056, and International Publication No. WO2020198273A2, all of which are incorporated herein by reference in their entireties.

The prosthetic valve 10 can be radially compressible and expandable between a radially compressed configuration and a radially expanded configuration. The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10.

The struts 24 can be pivotably coupled to one another at one or more pivot joints or pivot junctions 28 along the length of each strut. For example, in one example, each of the struts 24 can be formed with apertures at opposing ends of the strut and apertures spaced along the length of the strut. Respective hinges can be formed at the locations where struts 24 overlap each other via fasteners 38, such as rivets or pins that extend through the apertures. The hinges can allow the struts 24 to pivot relative to one another as the frame 12 is radially expanded or compressed, such as during assembly, preparation, or implantation of the prosthetic valve 10.

The frame struts and the components used to form the pivot joints of the frame 12 (or any frames described below) can be made of any of various suitable materials, such as stainless steel, a cobalt chromium alloy, or a nickel titanium alloy ("NiTi"), for example Nitinol. In some examples, the frame 12 can be constructed by forming individual components (e.g., the struts and fasteners of the frame) and then mechanically assembling and connecting the individual components together. Further details regarding the construction of the frame and the prosthetic valve are described in U.S. Pat. Nos. 10,603,165 10,869,759, and 10,806,573 and International Publication No. WO2020081893A1, all of which are incorporated herein by reference.

In the illustrated example, the prosthetic valve 10 can be mechanically expanded from the radially contracted configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated example, expansion and compression forces can be applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener 38 that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to foreshorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other examples, the actuators 50 can be reciprocating type actuators configured to apply axial directed forces to the frame to produce radial expansion and compression of the frame. For example, the rod 52 of each actuator can be fixed axially relative to the nut 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a sub-component of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated examples, the prosthetic valve 10 includes three such actuators 50, although a greater or fewer number of actuators could be used in other examples. The leaflets 20 can have commissure attachments members 64 that wrap around the sleeves 54 of the actuators 50. Further details of the actuators, locking mechanisms and delivery apparatuses for actuating the actuators can be found in U.S. Pat. No. 10,603,165, 10,806,573, and 10,430,488 and International Publication Nos. WO2021086933A2, and WO2021188476A1, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. In some examples, the prosthetic valve 10 can include an inner skirt (not shown) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in International Publication No. WO2020198273A2, which is incorporated herein by reference in its entirety.

FIG. 2 illustrates a delivery apparatus 100, according to one example, adapted to deliver a prosthetic heart valve 102, such as the illustrated prosthetic heart valve 10, described above. The prosthetic valve 102 can be releasably coupled to the delivery apparatus 100. It should be understood that the delivery apparatus 100 and other delivery apparatuses disclosed herein can be used to implant prosthetic devices other than prosthetic valves, such as stents or grafts.

The delivery apparatus 100 in the illustrated example generally includes a handle 104, a first elongated shaft 106 (which comprises an outer shaft in the illustrated example) extending distally from the handle 104, at least one actuator assembly 108 extending distally through the outer shaft 106. The at least one actuator assembly 108 can be configured to radially expand and/or radially collapse the prosthetic valve 102 when actuated.

Though the illustrated example shows two actuator assemblies 108 for purposes of illustration, it should be understood that one actuator 108 can be provided for each actuator on the prosthetic valve. For example, three actuator assemblies 108 can be provided for a prosthetic valve having three actuators. In other examples, a greater or fewer number of actuator assemblies can be present.

In some examples, a distal end portion 116 of the shaft 106 can be sized to house the prosthetic valve in its radially compressed, delivery state during delivery of the prosthetic valve through the patient's vasculature. In this manner, the distal end portion 116 functions as a delivery sheath or capsule for the prosthetic valve during delivery, The actuator assemblies 108 can be releasably coupled to the prosthetic valve 102. For example, in the illustrated example, each actuator assembly 108 can be coupled to a respective actuator of the prosthetic valve 102. Each actuator assembly 108 can comprise a support tube, an actuator member, and a locking tool. When actuated, the actuator assembly can transmit pushing and/or pulling forces to portions of the prosthetic valve to radially expand and collapse the prosthetic valve as previously described. The actuator assemblies 108 can be at least partially disposed radially within, and extend axially through, one or more lumens of the outer shaft 106. For example, the actuator assemblies 108 can extend through a central lumen of the shaft 106 or through separate respective lumens formed in the shaft 106.

The handle 104 of the delivery apparatus 100 can include one or more control mechanisms (e.g., knobs or other actuating mechanisms) for controlling different components of the delivery apparatus 100 in order to expand and/or deploy the prosthetic valve 102. For example, in the illustrated example the handle 104 comprises first, second, and third knobs 110, 112, and 114.

The first knob 110 can be a rotatable knob configured to produce axial movement of the outer shaft 106 relative to the prosthetic valve 102 in the distal and/or proximal directions in order to deploy the prosthetic valve from the delivery sheath 116 once the prosthetic valve has been advanced to a location at or adjacent the desired implantation location with the patient's body. For example, rotation of the first knob 110 in a first direction (e.g., clockwise) can retract the sheath 116 proximally relative to the prosthetic valve 102 and rotation of the first knob 110 in a second direction (e.g., counterclockwise) can advance the sheath 116 distally. In other examples, the first knob 110 can be actuated by sliding or moving the knob 110 axially, such as pulling and/or pushing the knob. In other examples, actuation of the first knob 110 (rotation or sliding movement of the knob 110) can produce axial movement of the actuator assemblies 108 (and therefore the prosthetic valve 102) relative to the delivery sheath 116 to advance the prosthetic valve distally from the sheath 116.

The second knob 112 can be a rotatable knob configured to produce radial expansion and/or contraction of the prosthetic valve 102. For example, rotation of the second knob 112 can move the actuator member and the support tube axially relative to one another. Rotation of the second knob 112 in a first direction (e.g., clockwise) can radially expand the prosthetic valve 102 and rotation of the second knob 112 in a second direction (e.g., counterclockwise) can radially collapse the prosthetic valve 102. In other examples, the second knob 112 can be actuated by sliding or moving the knob 112 axially, such as pulling and/or pushing the knob.

The third knob 114 can be a rotatable knob configured to retain the prosthetic heart valve 102 in its expanded configuration. For example, the third knob 114 can be operatively connected to a proximal end portion of the locking tool of each actuator assembly 108. Rotation of the third knob in a first direction (e.g., clockwise) can rotate each locking tool to advance the locking nuts to their distal positions to resist radial compression of the frame of the prosthetic valve, as described above. Rotation of the knob 114 in the opposite direction (e.g., counterclockwise) can rotate each locking tool in the opposite direction to decouple each locking tool from the prosthetic valve 102. In other examples, the third knob 114 can be actuated by sliding or moving the third knob 114 axially, such as pulling and/or pushing the knob.

Although not shown, the handle 104 can include a fourth rotatable knob operative connected to a proximal end portion of each actuator member. The fourth knob can be configured to rotate each actuator member, upon rotation of the knob, to unscrew each actuator member from the proximal portion of a respective actuator. As described above, once the locking tools and the actuator members are uncoupled from the prosthetic valve 102, they can be removed from the patient.

FIG. 3 illustrates an exemplary example of a prosthetic valve 200 comprising a frame 202 and one or more expansion and locking mechanisms 204. The frame 202 comprises a plurality of pivotably connected struts 206 defining an inflow end 208 (which is the distal end of the frame in the delivery configuration for the illustrated example) and an outflow end 210 (which is the proximal end of the frame in the delivery configuration for the illustrated example). The struts 206 are pivotably connected to each other at a plurality of junctions that permit pivoting of the struts relative to each other when the frame 202 is radially compressed and expanded, as described above in connection with prosthetic valve 10.

The prosthetic valve 200 can include a valvular structure (e.g., valvular structure 18) and inner and/or outer skirts, as previously described, although these components are omitted for purposes of illustration. The expansion and locking mechanisms 204 can be used to both radially expand the frame 202 and lock the frame in a radially expanded state.

FIG. 3 shows three expansion and locking mechanisms 204 mounted to the frame 202 and spaced apart from one another about the circumference of the frame. However, in other examples, a prosthetic valve can comprise any number of expansion and locking mechanisms 204. For example, in some examples, a prosthetic valve can comprise a single expansion and locking mechanism, or two expansion and locking mechanisms, or four expansion and locking mechanisms, etc. The expansion and locking mechanisms 204 can be placed at any position about the circumference of the frame 202. For example, in some examples, it can be advantageous to have two or more expansion and locking mechanisms situated adjacent to one another.

Figures 4, 5:
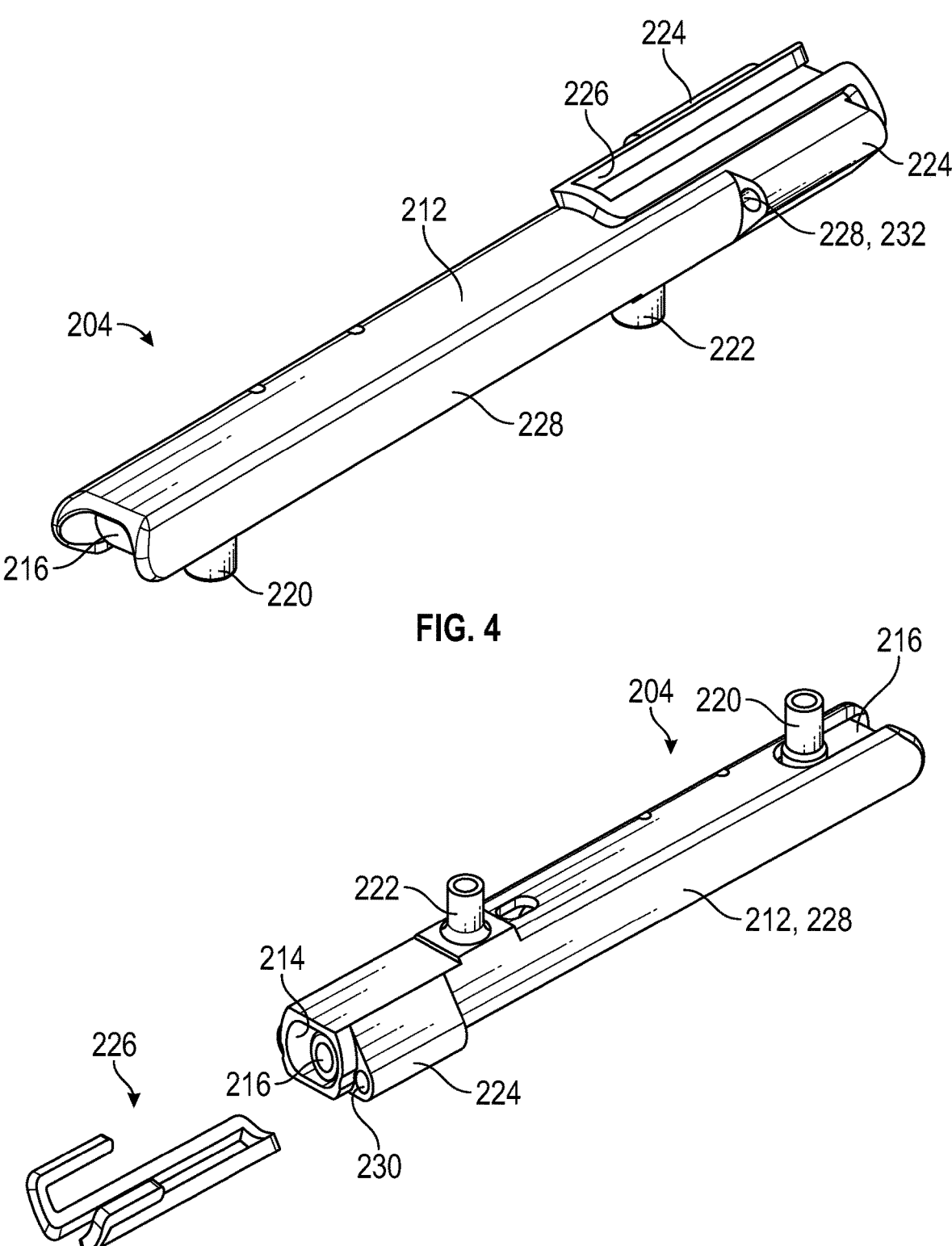
FIG. 4 is a perspective view of an expansion and locking mechanism of the prosthetic heart valve of FIG. 3.
FIG. 5 is a perspective view of the expansion and locking mechanism of FIG. 4 with the commissure attachment member removed.

Referring to FIGS. 4-5, each expansion and locking mechanism 204 can include a first or outer member 212 (also referred to as a sleeve) having an inner lumen, cavity, or bore 214, and a second or inner member 216 extending at least partially into the cavity 214. In some examples, the expansion and locking mechanisms 204 can comprise a locking member 218 (FIG. 10) configured to restrain the first and second members 212, 214 from movement relative to one another. Further details of the expansion and locking mechanisms, including examples of locking members, can be found in US Publication No. 2022/0257367 which is incorporated by reference herein in its entirety.

As best shown in FIG. 3, a distal end portion of the inner member 216 can be coupled to the frame 202 at a first location via a fastener 220 (FIG. 5) that is affixed to and extends radially from the distal end portion of the inner member 216. The fastener 220 can be, for example, a rivet or a pin. As shown, in some examples, the fastener 220 can extend through corresponding apertures at a junction of two overlapping struts 206 of frame 202 and can serve as a pivot pin around which the two struts 206 can pivot relative to one another and the inner member 216.

The outer member 212 can be coupled to the frame 202 at a second location, axially spaced from the first location. For example, in the illustrated example, the inner member 216 is secured to the frame 202 near the distal or inflow end 208 of the frame and the outer member 212 is secured to the frame 202 closer to or at the proximal or outflow end 210 of the frame, such as via a fastener 222 (e.g., a rivet or pint) (FIG. 5). The fastener 222 is affixed to and extends radially from the outer member 212 through corresponding apertures at a junction of two overlapping struts 206 and can serve as a pivot pin around which the two struts 206 can pivot relative to each other and the outer member 212. In some examples, an end cap or nut can be disposed over an end portion of each fastener 220, 222, or, in other examples, the fasteners 220, 222 can have flanged end portions sized to retain the fastener within the apertures.

Because the inner member 216 and the outer member 212 are secured to the frame 202 at axially spaced locations, movement of the inner member 216 and the outer member 212 axially with respect to one another in a telescoping manner can cause radial expansion or compression of the frame 202. For example, moving the inner member 216 proximally toward the outflow end 210 of the frame, while holding the outer member 212 in a fixed position and/or moving the outer member 212 distally toward the inflow end 208 of the frame can cause the frame 202 to foreshorten axially and expand radially. Conversely, moving the inner member 216 distally and/or moving the outer member 212 proximally causes the frame 202 to elongate axially and compress radially.

As shown in FIGS. 3-5, each expansion and locking mechanism 204 can comprise one or more lateral extensions 224. The lateral extensions 224 can be configured to couple a locking commissure attachment member 226 to secure a portion of the valvular structure to couple the valvular structure to the frame 202. Each lateral extension 224 can extend laterally from a side wall 228 of the outer member 212 and can have a length $L_1$ (FIG. 8). Each lateral extension can comprise an inner lumen or bore 228 (FIG. 4) including a first or outflow opening 230 (FIG. 5) and a second or inflow opening 232 (FIG. 4). In the illustrated example, each expansion and locking mechanism 204 has two lateral extensions 224, however, in other examples, each expansion and locking mechanism 204 can comprise any number of lateral extensions (including none) as desired.

As mentioned, each expansion and locking mechanism 204 can be configured to couple a respective commissure attachment member 226. Referring to FIG. 6, a commissure attachment member 226 can comprise a body portion 234 and one or more arms 236. In the illustrated example, the body portion 234 can be U-shaped member including first and second side members 238 defining a commissure opening 240 between them. When assembled with the frame 202, the body portion 234 can be oriented such that the opening of the U-shape faces the outflow end 210 of the frame 202, as shown in FIG. 3. Each arm 236 can have a laterally extending portion 242 coupled to the body portion 234 and an axially extending portion 244, such that the overall shape of the commissure attachment member 226 is substantially sinusoidal. Each commissure attachment member 226 can be formed, for example, using simpler processing and machining procedures such as laser cutting, waterjet cutting, 3D printing, etc.

As shown in FIGS. 6-7, the axially extending portion 244 of each arm 236 can terminate in a latching mechanism 246. The latching mechanism 246 can comprise a first member 248 and a second member 250 coupled together via a compliant hinge or joint 252. The compliant joint 252 can be configured to allow pivotable movement of the second member 250 and the first member 248 relative to one another via elastic body deformation of the joint 252.

Referring to FIG. 7, each compliant joint 252 can comprise a flexible neck portion 254 at least partially defining a C-shaped cutout 256 including a gap G between the first and second members 248, 250. In alternative examples, the cutout 256 can have other shapes, such as a V-shape, oval, square, etc., which are open at one end to define a gap G. The compliant joint 252 can be configured to bias the second member 250 away from the first member 248, as shown in FIG. 7. In other examples, other forms of compliant joints or flexure linkages can be utilized. Exemplary flexures and hinge types can include, for example, leaf-type hinges, beam-type hinges, flat-spring type hinges, circular flexures, elliptical flexures, corner-filleted flexures, cross-flexures flexures (also referred to as crossed leaf-type hinges), prismatic crossed hinges, notched hinges, multi-trapezoidal hinges (also referred to as butterfly hinges), filleted V-shaped flexures, cyclonoidal flexures, circularly curved beam flexures, spherical flexures, and/or selective compliance hinges. Further details of compliant hinges can be found, for example, in International Publication No. WO2022011080A1, which is incorporated by reference herein in its entirety.

The second member 250 can pivot relative to the first member 248 between an expanded or open position (FIG. 7) and a compressed position (FIG. 9B). As the second member 250 moves from the open position to the compressed position, the flexible neck portion 254 can deform or deflect and the gap G can narrow. Referring to FIG. 9B, the first and second members 248, 250 can each have a width narrower than a width $W_1$ of the axially-extending portion 244 of the arm 236, such that when the second member 250 is in the compressed position the latching mechanism 246 has an overall width $W_2$ less than or equal to the width $W_1$ of the axially-extending portion 244. In the illustrated example, the first member 248 can have a width $W_3$ that is greater than a width $W_4$ of the second member 250, however, in other examples the widths $W_3$ and $W_4$ of the first and second members 248, 250 can be equal, or the width $W_4$ of the second member can be greater than the width $W_3$ of the first member.

Referring to FIGS. 8-10, the commissure attachment member 226 can be coupled to the expansion and locking mechanism 204 in the following exemplary manner. As shown in FIG. 8, the commissure attachment member 226 can be disposed over the expansion and locking mechanism 204 such that the axially extending portion 244 of each arm 236 aligns with a respective first opening 230 of the lateral extensions 224. Thus aligned, the axially extending portion 244 can be inserted into the inner bore 228 of the lateral extension 224, as shown in FIG. 9A. As the axially extending portion 244 is inserted into the bore 228, the compliant joint 252 of the latching mechanism 246 deflects to pivot the second member 250 into the compressed position, as shown in FIG. 9B.

The axially extending portion 244 can continue to slide through the bore 228 until it exits the second opening 232. Once the second member 250 has fully emerged from the bore 228 it can bias outward, as shown in FIG. 10, such that an outflow edge 258 (FIG. 9B) of the second member 250 abuts an inflow edge 260 of the lateral extension 224, thereby preventing axial movement of the commissure attachment member 226 relative to the lateral extension 224 in a first direction (e.g., upwardly in the orientation shown in FIG. 10). This configuration can be referred to as the latching mechanism 246 being in the locked position. The length $L_2$ (FIG. 8) of the axially extending portion 244 can be selected such that it substantially corresponds to the length $L_1$ (FIG. 8) of the lateral extension 224 such that when the latching mechanism 246 is in the locked position, the laterally extending portion 242 of the arm 236 can abut the outflow edge 262 of the lateral extension 224, thereby preventing axial movement of the commissure attachment member 226 relative to the lateral extension 224 in a second direction (e.g., downwardly in the orientation shown in FIG. 10).

To remove the commissure attachment member 226 from the expansion and locking mechanism 204, the second member 250 can be pivoted (e.g., manually) toward the first member 248 into the compressed position and an upwardly directed force (e.g., in the orientation shown in FIG. 10) can be applied to the commissure attachment member 226 to move the compressed latching mechanism 246 through the bore 228 and thereby decouple the commissure attachment member 226 from the expansion and locking mechanism 204.

As shown in FIG. 11, each commissure attachment member 226 can have an overall curved shape. For example, the commissure attachment member 226 can curve radially outwardly such that a space S is defined between a radially outer surface 264 of the commissure attachment member and a radially inner surface 266 of the outer member 212. The curved shape can help couple portions of the valvular structure to the frame 202 by allowing folded portions of the valvular structure to be disposed within the space S.

As mentioned, prosthetic valve 200 can further comprise a valvular structure, similar to the valvular structure 18 shown in FIG. 1. The valvular structure can be configured to regulate the flow of blood through the prosthetic valve 200 from the inflow end portion 208 to the outflow end portion 210. The valvular structure can include, for example, a leaflet assembly comprising one or more leaflets 268, portions of which are shown in FIG. 12, made of flexible material. The leaflets 268 can be made in whole or in part, from biological material, bio-compatible synthetic materials, or other such materials. Suitable biological material can include, for example, bovine pericardium (or pericardium from other sources). The leaflets 268 can be secured to one another at their adjacent sides to form commissures, each which can be secured to a respective expansion and locking mechanism 204, via a commissure attachment member 226, as discussed further below. Each leaflet can have an inflow edge portion (also referred to as a cusp edge portion) that can be mounted to the frame and an outflow edge portion (also referred to as the free edge portion) that contacts respective outflow edges of the other leaflets during closure of the leaflets (e.g., during diastole). The cusp edge portion of each leaflet 268 terminates at its upper ends at two laterally projecting integral tabs 270.

Referring to FIGS. 12-15, in some examples, a valvular structure can be secured to the frame 202 in the following exemplary manner. During assembly, two adjacent tabs 270 can be coupled to a respective commissure attachment member 226 to form a commissure assembly 272, as shown in FIG. 13. FIG. 14 illustrates a cross-sectional view of a commissure assembly 272 coupled to an expansion and locking mechanism 204 in an exemplary configuration. The tabs 270 can be coupled to the commissure attachment member 226 by inserting the tabs 270 through the commissure opening 240 and folding each tab along the radially inner surface 266 of the expansion and locking mechanism 204 to form a first layer 274. Each tab 270 can then be folded back toward the commissure opening 240 to form a second layer 276 disposed between the first layer 274 and the radially outer surface 264 of the commissure attachment member 226. The first and second layers 274, 276 of each tab 270 can be coupled together by a respective first suture 278. The free ends of the tabs 270 can extend through the commissure opening 240 and be folded along a radially inner surface 280 of the commissure attachment member 226 to form a third layer 282, which can be secured to the first and second layers 274, 276 by a second suture 284.

As shown in FIG. 15, thus assembled, the commissure assembly 272 can be attached to the frame 202 by coupling the commissure attachment member 226 to the expansion and locking mechanism 204, as described previously. Such a configuration advantageously allows the commissure assemblies 272 to be pre-assembled prior to mounting to the frame 202, which advantageously simplifies the assembly process.

Referring to FIGS. 16-17, in another example, in lieu of or in addition to expansion and locking mechanisms 204, the prosthetic valve 200 can comprise expansion and locking mechanisms 300. Expansion and locking mechanisms 300 can be similar to expansion and locking mechanisms 204 (e.g., comprising an outer member 302 having an inner bore 304, an inner member disposed at least partially within the bore 304, and a locking member 306) except that expansion and locking mechanisms 300 can comprise one or more lateral extensions 308 and one or more angled protrusions 310. Expansion and locking mechanisms 300 can include the same features described above for expansion and locking mechanisms 204.

Lateral extensions 308 can be configured to couple a commissure attachment member 312 (FIG. 18) to secure a portion of the valvular structure to couple the valvular structure to the frame 202. Each lateral extension 308 can extend laterally from a side wall 314 of the outer member 302 and can have a length $L_3$ (FIG. 16). Each lateral extension 308 can comprise an inner lumen or bore 316 extending along the length $L_3$ of the lateral extension 308 and including a first opening 318 and a second opening 320 (FIG. 20). One or more of the lateral extensions 308 can be paired with a respective angled protrusion 310. Each angled protrusion 310 can extend laterally from the side wall 314 and can be spaced apart from the inflow edge 322 of the lateral extension 308 in an axial direction.

As shown in FIG. 16, the angled protrusion 310 can comprise an angled surface 324. The angled surface 324 can be spaced apart from the inflow edge 322 of the lateral extension 308 a first distance $D_1$ at a radially inner portion 326 of the angled protrusion 310, and can be spaced apart from the inflow edge 322 a second distance $D_2$ at a radially outer portion 328 of the angled protrusion 310. In other words, the angled surface 324 and the inflow edge 322 can define a channel 330 between them, and the width of the channel 330 can flare outwardly from the radially inner end to the radially outer end.

In the illustrated example, as shown in FIG. 17, only one of the lateral extensions 308 is paired with a respective angled protrusion 310. However, in other examples, each lateral extension 308 can be paired with a respective angled protrusion 310. In some examples, such as the illustrated example shown in FIG. 17, lateral extensions 308 that are not paired with a respective angled protrusion 310 can have a length $L_4$ greater than length $L_3$ (FIG. 16). In other examples, the unpaired lateral extensions (e.g., lateral extensions without a corresponding angled protrusion 310) can have the same length $L_3$ as the paired lateral extensions.

As mentioned, each expansion and locking mechanisms 300 can be configured to couple a respective commissure attachment member 312. Commissure attachment member 312 can be similar to commissure attachment member 226, except that in lieu of latching mechanism 246, commissure attachment member 312 can include a deflectable portion 344 configured to lock the commissure attachment member 312 in a selected position relative to the expansion and locking mechanism 300.

Referring to FIG. 18, a commissure attachment member 312 can comprise a body portion 332 and one or more arms 334. In the illustrated example, the body portion 332 can be U-shaped member including first and second side portions 336 defining a commissure opening 338 between them. When assembled with the frame 202, the body portion 332 can be oriented such that the opening of the U-shape faces the outflow end 210 of the frame 202. Each arm 334 can have a laterally extending portion 340 coupled to the body portion 332 and an axially extending portion 342 extending toward the inflow end of the frame 202 when the commissure attachment member 312 is coupled to the frame 202, such that the overall shape of the commissure attachment member 312 is substantially sinusoidal. Each commissure attachment member 312 can be formed, for example, using simpler processing and machining procedures such as laser cutting, waterjet cutting, 3D printing, etc. The inflow end portion of each axially extending portion 342 can be configured as a deflectable portion 344, which can be plastically deformable.

Referring to FIGS. 19-20, the commissure attachment member 312 can be coupled to the expansion and locking mechanism 300 in the following exemplary manner. As shown in FIG. 19, the commissure attachment member 312 can be disposed over the expansion and locking mechanism 300 such that the axially extending portion 342 of each arm 334 aligns with a respective first opening 318 of the lateral extension 308. Thus aligned, the axially extending portion 342 can be inserted through the inner bore 316 (FIG. 17) until the deflectable portion 344 contacts the angled surface 324.

As shown in FIG. 20, an axially directed force can be applied to the commissure attachment member 312 (e.g., as represented by arrow 346) to urge the deflectable portion 344 against the angled protrusion 310 such that the deflectable portion 344 deforms in a radially outward direction.

The axially directed force can continue to be applied until the laterally extending portion 340 abuts an outflow edge 348 of the lateral extension. So deformed, the deflectable portion 344 can prevent or mitigate axial movement of the commissure attachment member 312 in a first axial direction (e.g., upwardly in the orientation shown in FIG. 20). This configuration can be referred to as the deflectable portion 344 being in the locked position. The length $L_5$ (FIG. 19) of the axially extending portion 342 can be selected such that it substantially corresponds to the length $L_3$ (FIG. 16) of the lateral extension 308 such that when the deflectable portion 344 is in the locked position, the laterally extending portion 340 can abut the outflow edge 348 of the lateral extension 308, thereby preventing axial movement of the commissure attachment member 312 relative to the lateral extension 308 in a second direction (e.g., downwardly in the orientation shown in FIG. 20).

A valvular structure (e.g., similar to valvular structure 18 shown in FIG. 1) can be secured to the frame 202 using expansion and locking mechanism 300 and commissure attachment member 312 in the same manner as described previously for expansion and locking mechanism 204 and commissure attachment members 226. Namely, adjacent tabs 270 of the valvular structure can be coupled to a respective commissure attachment member 312 in the same manner as shown in FIG. 14 to form a commissure assembly and, so assembled, the commissure assembly can be attached to the frame 202 by coupling the commissure attachment member 312 to the expansion and locking mechanism 300, as described previously.

Advantageously, the commissure attachment members 226, 312 described herein (and therefore the commissure assemblies) can be locked into place relative to the expansion and locking mechanisms 204, 300 using only a sliding, axially-directed force, and without the need for any additional locking steps, thereby significantly simplifying the assembly procedure.

While the commissure attachment members 226, 312 are described herein with reference to expansion and locking mechanisms 204 and 300, it should be noted that the commissure attachment members 226, 312 can be coupled to any post of a frame having lateral extensions such as or similar to lateral extensions 224 and 308 described previously.

In some examples, it can be advantageous to secure both the upper portion (e.g., the outflow end portion) and the lower portion (e.g., the inflow end portion) of a commissure attachment member to a respective expansion and locking mechanism. Such examples can prevent or mitigate the risk of the commissure attachment member from moving axially relative to the expansion and locking mechanism (e.g., such that the arms of the commissure attachment member disengage the lateral extensions) during expansion of the prosthetic valve. Furthermore, securing the lower portion of the commissure attachment member to the expansion and locking mechanism can prevent or mitigate bending of the commissure attachment member under the radially-inwardly applied forces that occur during diastole.

Referring to FIGS. 21-23, in some examples, in lieu of or in addition to expansion and locking mechanisms 204 and 300, the prosthetic valve 200 can comprise expansion and locking mechanisms 400. As shown in FIG. 21, expansion and locking mechanisms 400 can be similar to expansion and locking mechanisms 204 and 300 (e.g., comprising an outer member 402 having an inner bore 404, an inner member disposed at least partially within the bore 404, and a locking member 406) except that expansion and locking mechanisms 400 can comprise first and second sets of lateral extensions 408, 410 configured to couple a commissure attachment member 412. Expansion and locking mechanisms 400 can include the same features described above for expansion and locking mechanisms 204 and 300.

As mentioned, and as shown in FIG. 21, each expansion and locking mechanism 400 can comprise a first set of lateral extensions 408 (e.g., comprising two lateral extensions) and a second set of lateral extensions 410 (e.g., comprising two lateral extensions). The first and second sets of lateral extensions 408, 410 can be configured to couple the commissure attachment member 412 to secure a portion of a valvular structure (e.g., similar to valvular structure 18 described previously) to couple the valvular structure to a frame, such as frame 202. Each lateral extension 408, 410 can extend laterally from a side wall 414 of the outer member 402. The first set of lateral extensions 408 can have a length $L_1$ and the second set of lateral extensions 410 can have a length $L_2$. In the illustrated example $L_2$ is less than $L_1$, however, in other examples $L_2$ can be greater than $L_1$ or the lengths can be equal. Each lateral extension 408, 410 can comprise an inner bore extending along the length of the extension and including an outflow opening 416. In some examples, the lateral extensions 408, 410 can include an inflow opening, however, in other examples the bore can be closed at the inflow end. The first and second sets of lateral extensions 408, 410 can be spaced apart from one another axially along the length of the expansion and locking mechanism 400.

As shown in the illustrated example, each first lateral extension 408 can be paired with a corresponding second lateral extension 410. In other words, respective first and second lateral extensions 408, 410 can be aligned with one another about the perimeter of the expansion and locking mechanism 400. In other examples, the expansion and locking mechanism 400 can comprise one or more unpaired lateral extensions, which can be either first or second lateral extensions 408, 410.

FIGS. 22-23 illustrate an exemplary commissure attachment member 412 configured to couple expansion and locking mechanism 400. Commissure attachment member 412 can comprise a body portion 418, one or more upper arms 420 (e.g., two in the illustrated example), and one or more lower arms 422 (e.g., two in the illustrated example). In the illustrated example, the body portion 418 can be a U-shaped member comprising a first side member 424 and a second side member 426 defining a commissure opening 428 between them. When assembled with the frame 202, the body portion 418 can be oriented such that the opening of the U-shape faces the outflow end 210 of the frame 202.

Each upper and lower arm 420, 422 can comprise a laterally extending portion 430 coupled to the body portion 418 and an axially extending portion 432 coupled to the laterally extending portion 430 and extending toward the inflow end 208 of the frame. In other examples, such as those shown in FIGS. 24-28, the axially extending portions of the lower set of arms can extend toward the outflow end of the frame. In some examples, the commissure attachment member 412 can have an overall curved shape such that the upper and lower arms curve radially outwardly relative to the frame.

In some examples, such as shown in FIG. 22, the commissure attachment member 412 can be formed by machining a tubular member (e.g., using laser cutting) to form the desired shape. In such examples, as shown, the upper and lower arms 408, 410 can extend from the body portion 418 in an arcuate manner. In other examples, as shown in FIG.

23, the commissure attachment member 412 can be formed from a flat metal sheet, for example, using stamping and bending. In such examples, as shown in FIG. 23, the upper and lower arms 408, 410 extend radially outwardly at a substantially orthogonal angle relative to the body portion 418.

Referring again to FIG. 21, the commissure attachment member 412 can be coupled to the expansion and locking mechanism 400 in the following exemplary manner. The commissure attachment member 412 can be disposed adjacent the expansion and locking mechanism 400 such that the axially extending portions 432 of the upper arms 420 are aligned with the outflow openings 416 of the first set lateral extensions 408 and such that the axially extending portions 432 of the lower arms 422 are aligned with the outflow openings 416 of the second set of lateral extensions 410. Thus aligned, the axially extending portions 432 of the first and second sets of arms 420, 422 can be inserted into the inner bores of the first and second sets of lateral extensions 408, 410, respectively, to secure the commissure attachment member 412 to the expansion and locking mechanism 400. In other examples, the lower arms 422 can be deflectable and can be configured to engage a projection extending from the expansion and locking mechanism 400 to secure the commissure attachment member 412 to the expansion and locking mechanism 400, similar to the method of attachment described for FIGS. 24-28.

Such a configuration advantageously secures both the upper portion 434 (e.g., the outflow portion) and the lower portion 436 (e.g., the inflow portion) of the commissure attachment member 412 to the expansion and locking member 400 thereby preventing or mitigating bending of the lower portion 436 relative to the upper portion 434 caused by force applied to the commissure attachment member 412 in a radially inward direction.

A valvular structure (e.g., similar to valvular structure 18 shown in FIG. 1) can be secured to the frame 202 using expansion and locking mechanism 400 and commissure attachment member 412 in the same manner as described previously for expansion and locking mechanisms 204 and 300. Namely, adjacent tabs 270 of the valvular structure can be coupled to a respective commissure attachment member 412 in the same manner as shown in FIG. 14 to form a commissure assembly and, so assembled, the commissure assembly can be attached to the frame 202 by coupling the commissure attachment member 412 to the expansion and locking mechanism 400, as described previously.

Referring now to FIGS. 24-27C, in some examples, in lieu of or in addition to expansion and locking mechanisms 204, 300, and 400, the prosthetic valve 200 can comprise expansion and locking mechanisms 500. Expansion and locking mechanisms 500 can be similar to expansion and locking mechanisms 204, 300, and 400 (e.g., comprising an outer member 502 having an inner bore 504, an inner member disposed at least partially within the bore 504, and a locking member 506), except that expansion and locking mechanisms 500 can comprise a set of lateral extensions 508 and one or more projections 510. Expansion and locking mechanisms 500 can include the same features described above for expansion and locking mechanisms 204, 300, and 400.

As shown in FIG. 24, each expansion and locking mechanism 500 can include a set of lateral extensions 508 (e.g., two lateral extensions 408 in the illustrated example), similar to lateral extensions 408 described previously, and one or more projections 510. The expansion and locking mechanism 500 can be configured to couple a commissure attachment member 512. The lateral extensions 508 can be configured to couple the upper arms 520 of a commissure attachment member 512, as described previously with respect to lateral extensions 408 and commissure attachment member 412, to secure the upper portion 516 of the commissure attachment member 512 to the expansion and locking mechanism. The one or more projections 510 can extend laterally from a side wall 534 of the outer member 502 and can be configured to secure the lower portion 536 of the commissure attachment member 512. As shown, each projection can comprise a ramped surface 538 and a lateral surface 540 (FIG. 27A) and can taper from a first width at the radially inner end 542 to a second, greater width at the radially outer end 544. The projections 510 can be spaced apart from the lateral extensions 508 axially along the length of the expansion and locking mechanism 500.

In the illustrated example, at least one lateral extension 508 is paired (e.g., aligned with around the perimeter of the expansion and locking mechanism) a respective projection 510. In some examples, each lateral extension 508 can be paired with a respective projection 510. In other examples, the expansion and locking mechanism 500 can comprise one or more unpaired lateral extensions.

FIGS. 25-26 illustrate an exemplary commissure attachment member 512. Commissure attachment member 512 is similar to commissure attachment member 412 (e.g., having a body portion 518, upper arms 520, lower arms 522, a first side member 524, a second side member 526, and a commissure opening 528) except that the axially-extending portions 532 of the lower arms 522 extend toward the outflow end 210 of the frame 202. Each upper and lower arm 520, 522 can comprise a laterally extending portion 530 coupled to the body portion 518 and an axially extending portion 532 coupled to the laterally extending portion.

Referring again to FIG. 24, the commissure attachment member 512 can be coupled to the expansion and locking mechanism 500 in the following exemplary manner. The commissure attachment member 512 can be disposed adjacent the expansion and locking mechanism 500 such that the axially extending portions 530 of the upper arms 520 are aligned with the outflow openings of the first set lateral extensions 508. Thus aligned, the axially extending portions 532 of the upper arms 520 can be inserted into the inner bores of the lateral extensions 508 to secure the upper portion 516 of the commissure attachment member 512 to the expansion and locking mechanism 500.

Referring now to FIGS. 27A-27C, the lower portion 536 of the commissure attachment member 512 can be secured to the expansion and locking mechanism 500 by applying a radially-outwardly directed force (e.g., as represented by arrow 546) to the lower portion 536 such that the axially extending portion 532 of a respective lower arm 522 slides along the ramped surface 538 of the projection 510. Referring to FIG. 27B, the axially extending portion 532 slides along the ramped surface 538 such that it deflects laterally in a first direction (e.g., as represented by arrow 548) allowing it to continue to advance along the ramped surface 538 as the projection 510 widens. Referring to FIG. 27C, once the axially extending portion 532 passes the radially outer ends 544 of the projection, it deflects laterally in a second direction (e.g., as represented by arrow 550) back toward its initial position. So positioned, the axially extending portion 532 can engage the lateral surface 540 of the projection 510 and the laterally extending portion 530 can engage a side surface 552, thereby securing the lower portion 536 of the commissure attachment member 512 to the expansion and locking mechanism 500.

A valvular structure (e.g., similar to valvular structure 18 shown in FIG. 1) can be secured to the frame 202 using expansion and locking mechanism 500 and commissure attachment member 512 in the same manner as described previously for expansion and locking mechanism 204 and commissure attachment members 226. Namely, adjacent tabs 270 of the valvular structure can be coupled to a respective commissure attachment member 512 in the same manner as shown in FIG. 14 to form a commissure assembly and, so assembled, the commissure assembly can be attached to the frame 202 by coupling the commissure attachment member 512 to the expansion and locking mechanism 500 as described.

Such a configuration advantageously secures both the upper and lower portions 516, 536 of the commissure attachment member 512 to the expansion and locking member 500, thereby preventing or mitigating bending of the commissure attachment member 512. The engagement of the axially extending portions 532 with the lateral surfaces 540 prevents or mitigates bending or deformation of the commissure attachment member 512 caused by force(s) applied to the member 512 in a radially inward direction, and the engagement of the laterally extending portions 530 with the side surfaces 552 prevents or mitigates axial movement of the commissure attachment member 512 relative to the expansion and locking mechanism 500.

Referring now to FIG. 28, in another example, in lieu of or in addition to projections 510, the expansion and locking mechanism 500 can comprise one or more projections 554. Each projection 554 can be oriented such that the ramped surface 546 extends in an axial direction, e.g., such that the projection 554 tapers from a first width at the outflow end 548 to a second, greater width at the inflow end 560. In such examples, to couple the lower portion 536 to the expansion and locking mechanism 500, the laterally extending portion 530 of a respective lower arm 522 can slide along the ramped surface 556 in the direction of arrow 562, deflecting in a first direction. Once past the inflow end portion 548 of the projection 554, the laterally extending portion 530 deflects in a second direction (e.g., returning to its original position). So positioned, the laterally extending portion 530 engages the surface at the inflow end 560 of the projection 554 and the axially extending portion 532 engages a side surface 564 of the projections 554, thereby securing the commissure attachment member 512 against radial and axial displacement relative to the expansion and locking mechanism 500.

Referring now to FIG. 29, in still another example, in lieu of or in addition to projections 510 and/or 554, the expansion and locking mechanism 500 can comprise projection 600. Projection 600 can be similar to projections 510 and 554, except that projection 600 does not comprise a ramped surface. As shown in FIG. 29, projection 600 extends laterally from the side wall 534 of the expansion and locking mechanism 500 and is shaped like a rectangular prism or cuboid. In such examples, the commissure attachment member 512 configured to engage projection 600 can comprise only a laterally extending portion 530 and no axially extending portion, as shown in FIG. 29.

To couple the commissure attachment member 512 to the expansion and locking mechanism 500 including projection 600, the upper portion 516 can be coupled as described previously. Once the upper portion has been inserted, a radially-outwardly directed force (e.g., as shown by arrow 602) can be applied to the lower portion 536 such that the laterally extending portions 530 are positioned adjacent an inflow surface 604 of the projection 600. So positioned, the engagement of the laterally extending portions 530 with the inflow surface 604 of the projection 600 can prevent axial displacement of the commissure attachment member 512 relative to the expansion and locking mechanism 500.

FIGS. 30-32 illustrate another example of a commissure attachment member 700. Commissure attachment member 700 can be similar to commissure attachment members 412 and 512, except that commissure attachment member 700 comprises a lower extension 702 having an engagement feature 704 configured to couple a corresponding feature on a radially inner surface of an expansion and locking mechanism (e.g., surface 566 of expansion and locking mechanism 500, shown in FIG. 24). The lower extension 702 can extend from the body portion 706 of the commissure attachment member 700 (e.g., toward an inflow end 208 of the frame 202 when the commissure attachment member is coupled to the expansion and locking mechanism). In some examples, the commissure attachment member 700 comprising a lower extension 702 can be formed by machining a tubular member (e.g., using laser cutting) to form the desired shape. In other examples, the lower extension 702 can be formed from a flat metal sheet, for example, using stamping and bending.

Commissure attachment member 700 can comprise a body portion 706 including a first side member 708 and a second side member 710, upper arms 712 each including a laterally extending portion 714 and an axially extending portion 716, and a commissure opening 718.

In some examples, the lower extension 702 can be formed integrally with the commissure attachment member 700 (e.g., they can be formed as one piece), as shown in FIGS. 30-32. In other examples, the lower extension 702 can be formed separately and can be coupled to the commissure attachment member 700 via, for example, welding, adhesives, mechanical means such as screws or pins, etc.

Referring to FIGS. 30-31, in some examples, the engagement feature 702 can be configured as an eyelet or aperture 720 extending through a thickness of the lower extension 702. In some examples, as shown in FIG. 30, the inflow end portion 722 of the lower extending 702 and the aperture 720 can have substantially rectangular shapes. In other examples, as shown in FIG. 31, the inflow end portion 722 and the aperture 720 can have substantially circular shapes. The aperture 720 can be configured to couple or engage a corresponding feature (e.g., a protrusion or recess, etc.) on the expansion and locking mechanism (e.g., expansion and locking mechanism 500 described previously). The lower extension 702 and the corresponding feature can engage in a locking manner (e.g., snap-fit, friction fit, clamping, etc.). For example, the expansion and locking mechanism can comprise a projection having a shape that corresponds to the shape of the aperture 720 such that the projection extends into the aperture 720 to couple the lower extension 702 to the expansion and locking mechanism.

In still other examples, as shown in FIG. 32, the engagement feature 704 can be configured as a bar 724. In the illustrated example, the bar 724 extends orthogonally relative to the lower extension 702 forming a T-shape. However, in other examples, the bar 724 can be positioned at any angle relative to the lower extension 702. The bar 724 can be configured to couple or engage a corresponding feature (e.g., a protrusion, recess, etc.) on the expansion and locking mechanism. The bar and corresponding feature can engage in a locking manner (e.g., snap-fit, friction fit, clamping connection, etc.). For example, the expansion and locking mechanism can comprise one or more projections positioned such that the lower extension 702 can be disposed between them and such that an outflow edge 726 of the bar 724 can engage the projections to retain the lower extension 702 relative to the expansion and locking mechanism.

In some examples, as shown in FIGS. 30-32, the lower extension 702 can comprise a biasing portion 728. The biasing portion 728 can be configured to bias the inflow end portion 722 of the lower extension (including the engagement feature 704) against the radially inner surface of the expansion and locking mechanism thereby facilitating the engagement between the engagement feature 704 and the corresponding feature of the expansion and locking mechanism.

The commissure attachment members disclosed herein (e.g., commissure attachment members 412, 512, and 700) advantageously prevent the lower portion of the commissure attachment member from moving relative to the frame during axial foreshortening of the prosthetic valve. Further, such configurations advantageously prevent or mitigate bending of the lower portion of the commissure attachment member relative to the upper portion, which can happen during the diastolic phase, where the leaflets extend radially inwardly to coapt with one another, thereby exerting stress (e.g., a radially-inwardly directed force) on the commissure attachment member.

While the commissure attachment members 412, 512, and 700 are described herein with reference to expansion and locking mechanisms 400 and 500, it should be noted that the commissure attachment members 412, 512, and 700 can be coupled to any post of a frame having lateral extensions, protrusions, and/or projections, similar to those described previously with respect to expansion and locking mechanisms 400 and 500.

Though the commissure attachment members herein are described with reference to mechanically-expandable valves comprising expansion and locking mechanisms, it should be noted that the commissure attachment members can be used with any type of valve. For example, commissure attachment members can be used with valves having a unitary lattice frames that are expandable and/or compressible via mechanical means, such as the valves shown in U.S. application Ser. No. 18/125,087, filed Mar. 22, 2023, which is incorporated by reference herein. In such examples, the lateral extensions, angled protrusions, and/or projections can be disposed on one or more axially-extending posts 404, for example, support posts 407 and/or actuator posts 406. It should be further be appreciated that the commissure attachment members disclosed herein can additionally be used with other types of transcatheter prosthetic valves, including balloon-expandable prosthetic heart valves, such as disclosed in U.S. Pat. No. 9,393,110, and 11,096,781 and U.S. Publication No. 2019/0365530, each of which is incorporated by reference herein, and self-expandable prosthetic heart valves, such as disclosed in U.S. Pat. No. 10,098,734, which is incorporated by reference herein. In such examples, the lateral extensions and/or angled protrusions can be disposed on one or more struts of the frame itself, or on axially-extending posts coupled to a radially inner and/or radially outer surface of the frame.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An implantable prosthetic device, comprising:
a radially expandable and compressible frame, the frame comprising an inflow end portion and an outflow end portion;
at least one expansion and locking mechanism comprising:
a first member coupled to the frame at a first location, the first member comprising first and second lateral extensions extending laterally from the first member, each lateral extension comprising an inner bore extending through a length of the lateral extension, a second member coupled to the frame at a second location spaced apart from the first location; and
at least one commissure attachment member having a first arm portion extending into the inner bore of the first lateral extension and a second arm portion extending into the inner bore of the second lateral extension, each commissure attachment member configured to couple a portion of a valvular structure to a respective expansion and locking mechanism.

Example 2. The prosthetic device of any example herein, particularly examples 1, wherein the commissure attachment member has a substantially sinusoidal shape.

Example 3. The prosthetic device of any example herein, particularly any one of examples 1-2, wherein the commissure attachment member has a body portion including two side members defining a commissure opening between them.

Example 4. The prosthetic device of any example herein, particularly example 3, wherein the first and second arm portions each comprise a laterally extending portion coupled to a respective side member and an axially extending portion coupled to the laterally extending portion.

Example 5. The prosthetic device of any example herein, particularly any one of examples 1-4, the commissure attachment member further comprising a latching mechanism movable between an open position and a compressed position, wherein when the latching mechanism is in the open position the commissure attachment member is restrained from movement relative to the expansion and locking mechanism.

Example 6. The prosthetic device of any example herein, particularly examples 5, wherein the latching mechanism comprises a first member coupled to a second member via a compliant joint, the first and second members being pivotable relative to one another to move the latching mechanism between the open position and the compressed position.

Example 7. The prosthetic device of any example herein, particularly examples 6, wherein the compliant joint is configured to bias the latching mechanism into the open position.

Example 8. The prosthetic device of any example herein, particularly any one of examples 1-4, wherein each expansion and locking mechanism further comprises an angled protrusion extending laterally from the first member and axially spaced from the first lateral extension, and wherein the commissure attachment member further comprises a deflectable portion configured to plastically deform into a locked position when the deflectable portion is urged against the angled protrusion.

Example 9. The prosthetic device of any example herein, particularly example 8, wherein when the deflectable portion is in the locked position the commissure attachment member is restrained from movement relative to the expansion and locking mechanism.

Example 10. The prosthetic device of any example herein, particularly any one of examples 1-9, further comprising a valvular structure including a plurality of leaflets each having opposing tabs, wherein each pair of adjacent tabs is coupled to a respective expansion and locking mechanism via a respective commissure attachment member.

Example 11. The prosthetic device of any example herein, particularly example 10, wherein each tab extends through a commissure opening in the commissure attachment member to form a first layer, folds back along its own respective length to form a second layer, and extends around a side portion of the commissure attachment member to form a third layer.

Example 12. The prosthetic device of any example herein, particularly example 11, further comprising a first suture extending through the first and second layers and a second suture extending through the first, second, and third layers.

Example 13. The prosthetic device of any example herein, particularly any one of examples 1-12, wherein the first lateral extension extends in a first lateral direction from a first side wall of the first member and the second lateral extension extends in a second lateral direction from a second side wall of the first member.

Example 14. The prosthetic device of any example herein, particularly any one of examples 1-13, further comprising a locking member coupled to the first member and configured to engage the second member to allow movement of the second member and the first member relative to one another in a first direction to allow radial expansion of the frame and prevent movement in a second direction to prevent radial compression of the frame.

Example 15. The prosthetic device of any example herein, particularly any one of examples 1-14, wherein the second member extends at least partially into the first member.

Example 16. The prosthetic device of any example herein, particularly any one of examples 1-15, wherein the commissure attachment member has an overall curved shape such that the first and second arm portions curve radially outwardly relative to a body portion.

Example 17. An implantable prosthetic device, comprising:
  a radially expandable and compressible frame, the frame comprising an inflow end portion and an outflow end portion;
  one or more expansion and locking mechanisms each comprising:
    a first member coupled to the frame at a first location, the first member comprising first and second lateral extensions extending laterally from the first member, each lateral extension comprising an inner bore extending through a length of the lateral extension, and
    a second member coupled to the frame at a second location spaced apart from the first location; and
  one or more commissure attachment members each coupled to a respective expansion and locking mechanism, each commissure attachment member comprising a first arm portion extending into the inner bore of a respective first lateral extension and a second arm portion extending into the inner bore of a respective second lateral extension, the first arm portion comprising a latching mechanism movable between an open position wherein the commissure attachment member is restrained from movement relative to the expansion and locking mechanism and a compressed position.

Example 18. The prosthetic device of any example herein, particularly example 17, wherein the commissure attachment member has a substantially sinusoidal shape.

Example 19. The prosthetic device of any example herein, particularly any one of examples 17-18, wherein the commissure attachment member has a body portion including two side members defining a commissure opening between them.

Example 20. The prosthetic device of any example herein, particularly example 19, wherein the first and second arm portions each comprise a laterally extending portion coupled to a respective side member and an axially extending portion coupled to the laterally extending portion.

Example 21. The prosthetic device of any example herein, particularly any one of examples 17-20, wherein the latching mechanism comprises a first member coupled to a second member via a compliant joint, the first and second members being pivotable relative to one another to move the latching mechanism between the open position and the compressed position.

Example 22. The prosthetic device of any example herein, particularly example 21, wherein the compliant joint is configured to bias the latching mechanism into the open position.

Example 23. The prosthetic device of any example herein, particularly any one of examples 17-22, further comprising a valvular structure including a plurality of leaflets each having opposing tabs, wherein pairs of adjacent tabs are coupled together to form a commissure, and wherein each commissure is coupled to a respective expansion and locking mechanism via a respective commissure attachment member.

Example 24. The prosthetic device of any example herein, particularly example 23, wherein each tab extends through a commissure opening in the commissure attachment member to form a first layer, folds back along its own respective length to form a second layer, and extends around a side portion of the commissure attachment member to form a third layer.

Example 25. The prosthetic device of any example herein, particularly example 24, further comprising a first suture extending through the first and second layers and a second suture extending through the first, second, and third layers.

Example 26. The prosthetic device of any example herein, particularly any one of examples 17-25, wherein the first lateral extension extends in a first lateral direction from a first side wall of the first member and the second lateral extension extends in a second lateral direction from a second side wall of the first member.

Example 27. The prosthetic device of any example herein, particularly any one of examples 17-26, further comprising a locking member coupled to the first member and configured to engage the second member to allow movement of the second member and the first member relative to one another in a first direction to allow radial expansion of the frame and prevent movement in a second direction to prevent radial compression of the frame.

Example 28. The prosthetic device of any example herein, particularly any one of examples 17-27, wherein the second member extends at least partially into the first member.

Example 29. The prosthetic device of any example herein, particularly any one of examples 17-28, wherein the commissure attachment member has an overall curved shape such that the first and second arm portions curve radially outwardly relative to a body portion.

Example 30. A method of assembling a prosthetic valve, comprising:

coupling adjacent tabs of adjacent leaflets of a valvular structure to a commissure attachment member, the commissure attachment member comprising a first arm portion and a second arm portion, the first arm portion comprising a latching mechanism movable between an open position and a compressed position;

aligning the commissure attachment member over an expansion and locking mechanism of a prosthetic valve such that the first and second arm portions of the commissure attachment member are aligned with respective inner bores of first and second lateral extensions extending laterally from the expansion and locking mechanism;

inserting the first and second arm portions through the inner bores of the first and second lateral extensions until the latching mechanism emerges from the inner bore;

allowing the latching mechanism to bias into the open position such that an outflow edge portion of the latching mechanism engages an inflow edge portion of the first lateral extension to inhibit movement of the commissure attachment member relative to the expansion and locking mechanism and such that the valvular structure is coupled to the expansion and locking mechanism.

Example 31. The method of any example herein, particularly example 30, wherein coupling the tabs of adjacent leaflets to the commissure attachment member comprises: inserting the tabs through a commissure opening in the commissure attachment member to form a first layer, folding the tabs back along their respective lengths to form a second layer disposed between the commissure attachment member and the first layer, inserting the tabs back through the commissure opening and wrapping them around the commissure attachment member to form a third layer, and coupling the first, second, and third layers to one another using one or more sutures.

Example 32. The method of any example herein, particularly example 31, further comprising coupling the first and second layer to one another using one or more additional sutures.

Example 33. An implantable prosthetic device, comprising:

a radially expandable and compressible frame, the frame comprising an inflow end portion and an outflow end portion;

at least one expansion and locking mechanism comprising:

a first member coupled to the frame at a first location, the first member comprising first and second lateral extensions extending laterally from the first member and an angled protrusion axially aligned with and axially spaced apart from the first lateral extension, each lateral extension comprising an inner bore extending through a length of the lateral extension, a second member coupled to the frame at a second location spaced apart from the first location;

at least one commissure attachment member having a first arm portion extending into the inner bore of the first lateral extension and a second arm portion extending into the inner bore of the second lateral extension, the first arm portion comprising a deflectable portion configured to plastically deform into a locked position when the deflectable portion is urged against the angled protrusion; and

wherein when in the locked position, the deflectable portion inhibits movement of the commissure attachment member relative to the expansion and locking mechanism.

Example 34. The prosthetic device of any example herein, particularly any one of example 33, wherein the commissure attachment member has a substantially sinusoidal shape.

Example 35. The prosthetic device of any example herein, particularly any one of examples 33-34, wherein the commissure attachment member has a body portion including two side members defining a commissure opening between them.

Example 36. The prosthetic device of any example herein, particularly any one of examples 35, wherein the first and second arm portions each comprise a laterally extending portion coupled to a respective side member and an axially extending portion coupled to the laterally extending portion.

Example 37. The prosthetic device of any example herein, particularly any one of examples 33-36, further comprising a valvular structure including a plurality of leaflets each having opposing tabs, wherein each pair of adjacent tabs is coupled to a respective expansion and locking mechanism via a respective commissure attachment member.

Example 38. The prosthetic device of any example herein, particularly example 37, wherein each tab extends through a commissure opening in the commissure attachment member to form a first layer, folds back along its own respective length to form a second layer, and extends around a side portion of the commissure attachment member to form a third layer.

Example 39. The prosthetic device any example herein, particularly example 38, further comprising a first suture extending through the first and second layers and a second suture extending through the first, second, and third layers.

Example 40. The prosthetic device of any example herein, particularly any one of examples 33-39, wherein the first lateral extension extends in a first lateral direction from a first side wall of the first member and the second lateral extension extends in a second lateral direction from a second side wall of the first member.

Example 41. The prosthetic device of any example herein, particularly any one of examples 33-40, further comprising a locking member coupled to the first member and configured to engage the second member to allow movement of the second member and the first member relative to one another in a first direction to allow radial expansion of the frame and prevent movement in a second direction to prevent radial compression of the frame.

Example 42. The prosthetic device of any example herein, particularly any one of examples 33-41, wherein the second member extends at least partially into the first member.

Example 43. The prosthetic device of any example herein, particularly any one of examples 31-29, wherein the commissure attachment member has an overall curved shape such that the first and second arm portions curve radially outwardly relative to a body portion.

Example 44. A method of assembling a prosthetic valve, comprising:

coupling adjacent tabs of adjacent leaflets of a valvular structure to a commissure attachment member, the commissure attachment member comprising a first arm portion and a second arm portion, the first arm portion comprising a deflectable portion;

aligning the commissure attachment member over an expansion and locking mechanism of a prosthetic valve such that the first and second arm portions of the commissure attachment member are aligned with respective inner bores of first and second lateral extensions extending laterally from the expansion and locking mechanism, the expansion and locking mechanism further comprising an angled protrusion axially aligned with and axially spaced from the first lateral extension;

inserting the first and second arm portions through the inner bores of the first and second lateral extensions until the deflectable portion emerges from the inner bore;

urging the deflectable portion against the angled protrusion to plastically deform the deflectable portion such that movement of the commissure attachment member relative to the expansion and locking member is inhibited and such that the valvular structure is coupled to the expansion and locking mechanism.

Example 45. The method of any example herein, particularly example 44, wherein coupling the tabs of adjacent leaflets to the commissure attachment member comprises: inserting the tabs through a commissure opening in the commissure attachment member to form a first layer, folding the tabs back along their respective lengths to form a second layer disposed between the commissure attachment member and the first layer, inserting the tabs back through the commissure opening and wrapping them around the commissure attachment member to form a third layer, and coupling the first, second, and third layers to one another using one or more sutures.

Example 46. The method of any example herein, particularly example 45, further comprising coupling the first and second layer to one another using one or more additional sutures.

Example 47. An implantable prosthetic device, comprising:

a radially expandable and compressible frame, the frame comprising an inflow end portion and an outflow end portion;

an expansion and locking mechanism comprising a member coupled to the frame at a first location, the member comprising a first set of lateral extensions disposed adjacent an outflow end of the member and a second set of lateral extensions axially spaced from the first set, each lateral extension comprising an inner bore extending into the lateral extension;

a commissure attachment member having a first set of arms each extending into a respective inner bore of a lateral extension of the first set of lateral extensions and a second set of arms each extending into a respective inner bore of a lateral extension of the second set of lateral extensions such that the commissure attachment member is restrained from movement relative to the expansion and locking mechanism in the radial and axial directions; and wherein each commissure attachment member is configured to couple a portion a valvular structure to the expansion and locking mechanism.

Example 48. The prosthetic device of any example herein, particularly example 47, wherein each arm of the first and second sets of arms comprises a laterally extending portion and an axially extending portion.

Example 49. The prosthetic device of any example herein, particularly example 47, wherein the axially extending portions extend toward the inflow end portion of the frame.

Example 50. The prosthetic device of any example herein, particularly example 47, wherein the axially extending portions of the arms of the first set of arms extends toward the inflow end portion of the frame, and wherein the axially extending portions of the arms of the second set of arms extends toward the outflow end portion of the frame.

Example 51. The prosthetic device of any example herein, particularly any one of examples 47-50, wherein the commissure attachment member has a body portion including two side members defining a commissure opening between them.

Example 52. The prosthetic device of any example herein, particularly any one of examples 47-51, wherein the expansion and locking mechanism is a first expansion and locking mechanism, wherein the prosthetic device further comprises second and third expansion and locking mechanisms, and wherein the first, second, and third expansion and locking mechanisms are spaced circumferentially about the frame relative to one another.

Example 53. The prosthetic device of any example herein, particularly any one of examples 47-52, further comprising a valvular structure including a plurality of leaflets each having opposing tabs, wherein each pair of adjacent tabs is coupled to a respective expansion and locking mechanism via a respective commissure attachment member.

Example 54. The prosthetic device of any example herein, particularly example 53, wherein each tab extends through a commissure opening in the commissure attachment member to form a first layer, folds back along its own respective length to form a second layer, and extends around a side portion of the commissure attachment member to form a third layer.

Example 55. The prosthetic device of any example herein, particularly any one of examples 47-54, wherein the commissure attachment member has an overall curved shape such that the first and second arm portions curve radially outwardly relative to a body portion.

Example 56. The prosthetic device of any example herein, particularly any one of examples 47-55, wherein the member is a first member and wherein the expansion and locking mechanism further comprises a second member extending at least partially into the first member, the second member coupled to the frame at a location spaced apart from the first location.

Example 57. The prosthetic device of any example herein, particularly example 56, further comprising a locking member coupled to the first member and configured to engage the second member to allow movement of the second member and the first member relative to one another in a first direction to allow radial expansion of the frame and prevent movement in a second direction to prevent radial compression of the frame.

Example 58. A method of assembling a prosthetic valve, comprising:

coupling adjacent tabs of adjacent leaflets of a valvular structure to a commissure attachment member, the commissure attachment member comprising a first set of arms and a second set of arms axially spaced from the first set of arms, each arm comprising a laterally extending portion and an axially extending portion;

aligning the commissure attachment member over an expansion and locking mechanism of a prosthetic valve such that the first set of arms are aligned with respective inner bores of a first set of lateral extensions extending laterally from the expansion and locking mechanism and such that the second set of arms are aligned with respective inner bores of a second set of lateral extensions extending laterally from the expansion and locking mechanism, the second set of lateral extensions being axially spaced from the first set of lateral extensions; and inserting the axially extending portions of the first set of arms into the respective inner bores of the first set of lateral extensions and the axially extending portions of the second set of arms into the respective inner bores of the second set of lateral extensions, such that the commissure attachment member is restrained from movement relative to the expansion and locking mechanism in the radial and axial directions.

Example 59. The method of any example herein, particularly example 58, wherein the axially extending portions extend toward the inflow end portion of the frame.

Example 60. The method of any example herein, particularly example 58, wherein the axially extending portions of the arms of the first set of arms extends toward the inflow end portion of the frame, and wherein the axially extending portions of the arms of the second set of arms extends toward the outflow end portion of the frame.

Example 61. The method of any example herein, particularly any one of examples 58-60, wherein coupling the tabs of adjacent leaflets to the commissure attachment member comprises:

inserting the tabs through a commissure opening in the commissure attachment member to form a first layer, folding the tabs back along their respective lengths to form a second layer disposed between the commissure attachment member and the first layer, inserting the tabs back through the commissure opening and wrapping them around the commissure attachment member to form a third layer, and coupling the first, second, and third layers to one another using one or more sutures.

Example 62. An implantable prosthetic device, comprising:

a radially expandable and compressible frame, the frame comprising an inflow end portion, an outflow end portion, and a commissure post comprising a first set of lateral extensions disposed adjacent an outflow end of the commissure post and a second set of lateral extensions spaced apart from the first set, each lateral extension comprising an inner bore;

a commissure attachment member having a first set of arms each extending into a respective inner bore of a lateral extension of the first set of lateral extensions and a second set of arms each extending into a respective inner bore of a lateral extension of the second set of lateral extensions such that the commissure attachment member is restrained from movement relative to the commissure post in the radial and axial directions; and wherein each commissure attachment member is configured to couple a portion a valvular structure to a respective commissure post.

Example 63. The prosthetic device of any example herein, particularly example 62, wherein each arm of the first and second sets of arms comprises a laterally extending portion and an axially extending portion.

Example 64. The prosthetic device of any example herein, particularly example 63, wherein the axially extending portions extend toward the inflow end portion of the frame.

Example 65. The prosthetic device of any example herein, particularly example 63, wherein the axially extending portions of the arms of the first set of arms extends toward the inflow end portion of the frame, and wherein the axially extending portions of the arms of the second set of arms extends toward the outflow end portion of the frame.

Example 66. An implantable prosthetic device, comprising:

a radially expandable and compressible frame, the frame comprising an inflow end portion and an outflow end portion;

an expansion and locking mechanism comprising a first member coupled to the frame at a first location, the member comprising one or more lateral extensions disposed adjacent an outflow end of the first member and one or more projections extending from a side wall of the expansion and locking mechanism and axially spaced from the lateral extensions, each lateral extension comprising an inner bore extending into the lateral extension;

a commissure attachment member having one or more first arms each extending into a respective inner bore of a lateral extension and one or more second arms each configured to engage a respective projection such that such that the commissure attachment member is restrained from movement relative to the expansion and locking mechanism in the radial and axial directions, each first and second arm comprising a laterally extending portion and an axially extending portion coupled to the laterally extending portion; and wherein each commissure attachment member is configured to couple a portion a valvular structure to the expansion and locking mechanism.

Example 67. The prosthetic device of any example herein, particularly example 66, wherein the one or more projections each comprise an angled surface such that the projection tapers from a first thickness at a radially inner end portion to a second, greater thickness at a radially outer end portion.

Example 68. The prosthetic device of any example herein, particularly any one of examples 66-67, wherein a radially inner surface of a respective axially extending portion of the one or more second arms engages a radially outer surface of a respective projection to restrain the commissure attachment member from radial movement relative to the expansion and locking mechanism.

Example 69. The prosthetic device of any example herein, particularly any one of examples 66-68, wherein the axially extending portions extend toward the inflow end portion of the frame.

Example 70. The prosthetic device of any example herein, particularly any one of examples 66-68, wherein the axially extending portions of the first arms extend toward the inflow end portion of the frame, and wherein the axially extending portions of the arms of the second set of arms extends toward the outflow end portion of the frame.

Example 71. The prosthetic device of any example herein, particularly example 70, wherein an outflow surface of a respective laterally extending portion of the one or more second arms engages an inflow outer surface of a respective projection to restrain the commissure attachment member from axial movement relative to the expansion and locking mechanism.

Example 72. The prosthetic device of any example herein, particularly any one of examples 66-71, wherein each projection tapers from a first thickness at a radially inner end portion to a second, greater thickness at a radially outer end portion.

Example 73. The prosthetic device of any example herein, particularly any one of examples 66-71, wherein each projection tapers from a first thickness at an outflow end portion to a second, greater thickness at an inflow end portion.

Example 74. The prosthetic device of any example herein, particularly any one of examples 66-73, wherein the one or more second arms are plastically deformable such that they can bend radially outwardly and return to an unbent position.

Example 75. The prosthetic device of any example herein, particularly any one of examples 66-74, wherein the commissure attachment member has a body portion including two side members defining a commissure opening between them.

Example 76. The prosthetic device of any example herein, particularly any one of examples 66-75, wherein the expansion and locking mechanism is a first expansion and locking mechanism, wherein the prosthetic device further comprises second and third expansion and locking mechanisms, and wherein the first, second, and third expansion and locking mechanisms are spaced circumferentially about the frame relative to one another.

Example 77. The prosthetic device of any example herein, particularly any one of examples 66-76, further comprising a valvular structure including a plurality of leaflets each having opposing tabs, wherein each pair of adjacent tabs is coupled to a respective expansion and locking mechanism via a respective commissure attachment member.

Example 78. The prosthetic device of any example herein, particularly example 77, wherein each tab extends through a commissure opening in the commissure attachment member to form a first layer, folds back along its own respective length to form a second layer, and extends around a side portion of the commissure attachment member to form a third layer.

Example 79. The prosthetic device of any example herein, particularly any one of examples 66-78, wherein the commissure attachment member has an overall curved shape such that the first and second arm portions curve radially outwardly relative to a body portion.

Example 80. The prosthetic device of any example herein, particularly any one of examples 66-79, wherein the member is a first member and wherein the expansion and locking mechanism further comprises a second member extending at least partially into the first member, the second member coupled to the frame at a location spaced apart from the first location.

Example 81. The prosthetic device of any example herein, particularly example 80, further comprising a locking member coupled to the first member and configured to engage the second member to allow movement of the second member and the first member relative to one another in a first direction to allow radial expansion of the frame and prevent movement in a second direction to prevent radial compression of the frame.

Example 82. A method of assembling a prosthetic valve, comprising:

coupling adjacent tabs of adjacent leaflets of a valvular structure to a commissure attachment member, the commissure attachment member comprising a first set of arms and a second set of arms axially spaced from the first set of arms, each arm comprising a laterally extending portion and an axially extending portion;

aligning the commissure attachment member over an expansion and locking mechanism of a prosthetic valve such that the first set of arms are axially aligned with respective inner bores of a set of lateral extensions extending laterally from the expansion and locking mechanism and such that the second set of arms are laterally aligned with respective projections extending laterally from the expansion and locking mechanism, the projections being axially spaced from the set of lateral extensions and each comprising an angled surface;

inserting the axially extending portions of the first set of arms into the respective inner bores of the set of lateral extensions, thereby restraining an outflow end portion of the commissure attachment member from radial movement relative to the expansion and locking mechanism; and applying a force to an inflow end portion of the commissure attachment member such the second set of arms engages the projections, thereby restraining the inflow end portion of the commissure attachment member from radial movement relative to the expansion and locking mechanism.

Example 83. The method of any example herein, particularly example 82, wherein each projection tapers from a first thickness at a radially inner end portion to a second, greater thickness at a radially outer end portion.

Example 84. The method of any example herein, particularly example 83, wherein applying a force to the commissure attachment member such that the second set of arms engage the projections comprises:

applying a radially inwardly directed force to an inflow end portion of the commissure such that each axially extending portion slides along a respective angled surface causing the axially extending portions deflect laterally outwardly, and allowing each axially extending portion to deflect laterally inwardly once it has passed a radially outer end portion of the respective projection.

Example 85. The method of any example herein, particularly example 82, wherein each projection tapers from a first thickness at an outflow end portion to a second, greater thickness at an inflow end portion.

Example 86. The method of any example herein, particularly example 85, wherein applying a force to the commissure attachment member such that the second set of arms engage the respective projections comprises:

applying an axially directed force to the commissure attachment member such that each laterally extending portion slides along a respective angled surface such that the axially extending portions deflect laterally outwardly, and allowing each axially extending portion to deflect laterally inwardly once it has passed a radially outer end portion of the respective projection.

Example 87. The method of any example herein, particularly any one of examples 82-86, wherein a radially inner surface of a respective axially extending portion engages a radially outer surface of a respective projection to prevent radial movement of the inflow end portion of the commissure attachment member relative to the expansion and locking mechanism.

Example 88. The method of any example herein, particularly any one of examples 82-87, wherein an outflow surface of a respective laterally extending portion engages an inflow surface of a respective projection to prevent axial movement of the commissure attachment member relative to the expansion and locking mechanism.

Example 89. An implantable prosthetic device, comprising:

a radially expandable and compressible frame, the frame comprising an inflow end portion and an outflow end portion;

an expansion and locking mechanism comprising a first member coupled to the frame at a first location, the member comprising a first set of lateral extensions disposed adjacent an outflow end of the first member and one or more projections extending from a side wall of the expansion and locking mechanism and axially spaced from the lateral extensions, each lateral extension comprising an inner bore extending into the lateral extension;

a commissure attachment member having one or more of first arms each extending into a respective inner bore of a lateral extension of the first set of lateral extensions and one or more second arms each configured to engage a respective projection of the one or more projections such that such that the commissure attachment member is retained from movement relative to the expansion and locking mechanism in the axial direction, each first and second arm comprising a laterally extending portion, the first arms further comprising an axially extending portion coupled to the laterally extending portion; and wherein each commissure attachment member is configured to couple a portion a valvular structure to the expansion and locking mechanism.

Example 90. The prosthetic device of any example herein, particularly example 89, wherein the projections have a rectangular prism shape.

Example 91. The prosthetic device of any example herein, particularly any one of examples 89-90, wherein an outflow surface of a laterally extending portion of each second arm engages an inflow surface of the projection to retain the commissure attachment member against movement in the axial direction.

Example 92. An implantable prosthetic device, comprising:

a radially expandable and compressible frame, the frame comprising an inflow end portion and an outflow end portion;

an expansion and locking mechanism comprising a member coupled to the frame at a first location, the member comprising first and second lateral extensions disposed adjacent an outflow end of the first member and an engagement feature spaced apart from the first and second lateral extensions, each lateral extension comprising a bore extending into the lateral extension;

a commissure attachment member having a first and second arms each extending into a respective inner bore of the first and second lateral extensions and a lower extension extending toward the inflow end portion of the frame and comprising a corresponding engagement feature coupled to the engagement feature of the expansion and locking mechanism; and wherein each commissure attachment member is configured to couple a portion a valvular structure to the expansion and locking mechanism.

Example 93. The prosthetic device of any example herein, particularly example 92, wherein the commissure attachment member is restrained from axial movement relative to the expansion and locking mechanism via the coupling of the corresponding engagement features.

Example 94. The prosthetic device of any example herein, particularly any one of examples 92-93, wherein the corresponding engagement feature comprises an aperture.

Example 95. The prosthetic device of any example herein, particularly example 94, wherein the aperture has a circular shape.

Example 96. The prosthetic device of any example herein, particularly example 95, wherein the engagement feature comprises a cylindrical protrusion sized to fit within the aperture.

Example 97. The prosthetic device of any example herein, particularly example 94, wherein the aperture has a rectangular shape.

Example 98. The prosthetic device of any example herein, particularly example 97, wherein the engagement feature comprises a rectangular protrusion sized to fit within the aperture.

Example 99. The prosthetic device of any example herein, particularly any one of examples 92-93, wherein the corresponding engagement feature comprises a bar extending perpendicularly to the lower extension.

Example 100. The prosthetic device of any example herein, particularly examples 92-99, wherein the lower extension comprises a biasing portion configured to bias the corresponding engagement feature against a radially inner surface of the expansion and locking mechanism.

Example 101. The prosthetic device of any example herein, particularly examples 92-100, wherein the first and second arms each comprise axially extending portions extending toward the inflow end portion of the frame.

Example 102. The prosthetic device of any example herein, particularly examples 92-101, wherein the engagement feature laterally from a radially inner surface of the expansion and locking mechanism.

Example 103. The prosthetic device of any example herein, particularly examples 92-102, wherein the commissure attachment member has a body portion including two side members defining a commissure opening between them.

Example 104. The prosthetic device of any example herein, particularly examples 92-103, wherein the expansion and locking mechanism is a first expansion and locking mechanism, wherein the prosthetic device further comprises second and third expansion and locking mechanisms, and wherein the first, second, and third expansion and locking mechanisms are spaced circumferentially about the frame relative to one another.

Example 105. The prosthetic device of any example herein, particularly examples 92-104, further comprising a valvular structure including a plurality of leaflets each having opposing tabs, wherein each pair of adjacent tabs is coupled to a respective expansion and locking mechanism via a respective commissure attachment member.

Example 106. A method of assembling a prosthetic valve, comprising:

coupling adjacent tabs of adjacent leaflets of a valvular structure to a commissure attachment member, the commissure attachment member comprising a first and second arms, each arm comprising a laterally extending portion and an axially extending portion, and a lower extension comprising an engagement feature;

aligning the commissure attachment member over an expansion and locking mechanism of a prosthetic valve such that the first and second arms are axially aligned with respective inner bores of first and second lateral extensions extending laterally from the expansion and locking mechanism and such that the engagement feature is aligned with a corresponding engagement feature on a radially inner surface of the expansion and locking mechanism;

inserting the axially extending portions of the first and second arms into the respective inner bores of the first and second lateral extensions, thereby restraining an outflow end portion of the commissure attachment member from radial movement relative to the expansion and locking mechanism; and applying a force to an inflow end portion of the commissure attachment member such the engagement feature engages the corresponding engagement feature of the expansion and locking mechanism, thereby restraining the inflow end portion of the commissure attachment member from movement relative to the expansion and locking mechanism.

Example 107. The method of any example herein, particularly example 106, wherein the engagement feature is an aperture and the corresponding engagement feature is a protrusion configured to fit within the aperture.

Example 108. An implantable prosthetic device, comprising:

a radially expandable and compressible frame, the frame comprising an inflow end portion, an outflow end portion, and a post, the post comprising first and second lateral extensions disposed adjacent an outflow end of the post and one or more projections extending from a side wall of the post and axially spaced from the lateral extensions, each lateral extension comprising an inner bore; and a commissure attachment member having a first set of arms, each extending into the inner bore of a respective lateral extension, and a second set of arms, each configured to engage a respective projection such that such that the commissure attachment member is restrained from movement relative to the post in the radial and axial directions, each first and second arm comprising a laterally extending portion and an axially extending portion coupled to the laterally extending portion, wherein the commissure attachment member is configured to couple a portion of a valvular structure to the post.

Example 109. An implantable prosthetic device, comprising:

a radially expandable and compressible frame, the frame comprising an inflow end portion, an outflow end portion, and a post, the post comprising first and second lateral extensions disposed adjacent an outflow end of the post and an engagement feature spaced apart from the first and second lateral extensions, each lateral extension comprising an inner bore extending into the lateral extension;

a commissure attachment member having a first and second arms each extending into a respective inner bore of the first and second lateral extensions and a lower extension extending toward the inflow end portion of the frame and comprising a corresponding engagement feature coupled to the engagement feature of the post; and wherein the commissure attachment member is configured to couple a portion of a valvular structure to the post.

Example 110. An implantable prosthetic device, comprising:

a radially expandable and compressible frame, the frame comprising an inflow end portion, an outflow end portion, and a post, the post comprising a first lateral extension disposed adjacent an outflow end of the member and a second lateral extension axially spaced from the first lateral extension;

a commissure attachment member having a first arm extending into an inner bore of the first lateral extension and a second arm extending into an inner bore of the second lateral extension such that the commissure attachment member is restrained from movement relative to the post in the radial and axial directions; and wherein the commissure attachment member is configured to couple a portion of a valvular structure to the post.

Example 111. An implantable prosthetic device, comprising:

a radially expandable and compressible frame, the frame comprising an inflow end portion, an outflow end portion, and a post, the post comprising a lateral extension disposed adjacent an outflow end of the post and a projection extending from a side wall of the post and axially spaced from the lateral extension, the lateral extension comprising an inner bore;

a commissure attachment member having a first arm extending into the inner bore of the lateral extension and a second arm configured to engage the projection such that such that the commissure attachment member is restrained from movement relative to the post in the radial and axial directions, the first and second arms comprising a laterally extending portion and an axially extending portion coupled to the laterally extending portion; and wherein the commissure attachment member is configured to couple a portion of a valvular structure to the post.

Example 112. An implantable prosthetic device, comprising:

a radially expandable and compressible frame, the frame comprising an inflow end portion, an outflow end portion, and a post, the post comprising a lateral extension disposed adjacent an outflow end of the post and an engagement feature spaced apart from the lateral extension, the lateral extension comprising an inner bore;

a commissure attachment member having a first arm extending into an inner bore of the lateral extension and a lower extension extending toward the inflow end portion of the frame and comprising a corresponding engagement feature coupled to the engagement feature of the post; and wherein the commissure attachment member is configured to couple a portion of a valvular structure to the post.

Example 113. An implantable prosthetic device, comprising:

a radially expandable and compressible frame, the frame comprising an inflow end portion and an outflow end portion;

an expansion and locking mechanism comprising a member coupled to the frame at a first location, the first member comprising first and second lateral extensions extending laterally from the first member, each lateral extension comprising an inner bore extending through a length of the lateral extension; and a commissure attachment member having a first arm portion extending into the inner bore of the first lateral extension and a second arm portion extending into the inner bore of the second lateral extension, the commissure attachment member configured to couple a portion of a valvular structure to the expansion and locking mechanism.

Example 114. The prosthetic device of any example herein, particularly example 113, wherein the commissure attachment member has a substantially sinusoidal shape.

Example 115. The prosthetic device of any example herein, particularly any one of examples 113-114, the commissure attachment member further comprising a latching mechanism movable between an open position and a compressed position, wherein when the latching mechanism is in the open position the commissure attachment member is restrained from movement relative to the expansion and locking mechanism.

Example 116. The prosthetic device of any example herein, particularly example 115, wherein the latching mechanism comprises a first member coupled to a second member via a compliant joint, the first and second members being pivotable relative to one another to move the latching mechanism between the open position and the compressed position.

Example 117. The prosthetic device of any example herein, particularly example 116, wherein the compliant joint is configured to bias the latching mechanism into the open position.

Example 118. The prosthetic device of any example herein, particularly any one of examples 113-117, wherein the first and second lateral extensions are a first set of lateral extensions and the member further comprises a second set of lateral extensions each having an inner bore; and wherein the first and second arm portions are a first set of arm portions and the commissure attachment member further comprises a second set of arm portions each extending into a respective inner bore of the second set of lateral extensions such that the commissure attachment member is restrained from movement relative to the expansion and locking mechanism in the radial and axial directions.

Example 119. The prosthetic device of any example herein, particularly any one of examples 113-118, wherein each arm portion comprises a laterally extending portion and an axially extending portion.

Example 120. The prosthetic device of any example herein, particularly example 119, wherein the axially extending portions extend toward the inflow end portion of the frame.

Example 121. The prosthetic device of any example herein, particularly example 119, wherein the axially extending portions of the arms of the first set of arms extends toward the inflow end portion of the frame, and wherein the axially extending portions of the arms of the second set of arms extends toward the outflow end portion of the frame.

Example 122. The prosthetic device of any example herein, particularly any one of examples 113-121, wherein the commissure attachment member has a body portion including two side members defining a commissure opening between them.

Example 123. The prosthetic device of any example herein, particularly any one of examples 113-122, wherein the expansion and locking mechanism is a first expansion and locking mechanism, wherein the prosthetic device further comprises second and third expansion and locking mechanisms, and wherein the first, second, and third expansion and locking mechanisms are spaced circumferentially about the frame relative to one another.

Example 124. The prosthetic device of any example herein, particularly any one of examples 113-123, further comprising a valvular structure including a plurality of leaflets each having opposing tabs, wherein each pair of adjacent tabs is coupled to a respective expansion and locking mechanism via a respective commissure attachment member.

Example 125. The prosthetic device of any example herein, particularly example 124, wherein each tab extends through a commissure opening in the commissure attachment member to form a first layer, folds back along its own respective length to form a second layer and extends around a side portion of the commissure attachment member to form a third layer.

Example 126. The prosthetic device of any example herein, particularly any one of examples 113-125, wherein the commissure attachment member has an overall curved shape such that the first and second arm portions curve radially outwardly relative to a body portion.

Example 127. The prosthetic device of any example herein, particularly any one of examples 113-127, wherein the member is a first member and wherein the expansion and locking mechanism further comprises a second member extending at least partially into the first member, the second member coupled to the frame at a location spaced apart from the first location.

Example 128. The prosthetic device of any example herein, particularly example 127, further comprising a locking member coupled to the first member and configured to engage the second member to allow movement of the second member and the first member relative to one another in a first direction to allow radial expansion of the frame and prevent movement in a second direction to prevent radial compression of the frame.

In view of the many possible examples to which the principles of the disclosure may be applied, it should be recognized that the illustrated examples are only preferred examples and should not be taken as limiting the scope. Rather, the scope is defined by the following claims. We therefore claim all that comes within the scope and spirit of these claims.

We claim:

1. An implantable prosthetic device, comprising:
a radially expandable and compressible frame, the frame comprising an inflow end portion and an outflow end portion;
an expansion and locking mechanism comprising a member coupled to the frame at a first location, the member comprising first and second lateral extensions extending laterally from the member, each lateral extension comprising an inner bore extending through a length of the lateral extension; and
a commissure attachment member having a first arm portion extending into the inner bore of the first lateral extension and a second arm portion extending into the inner bore of the second lateral extension, the commissure attachment member configured to couple a portion of a valvular structure to the expansion and locking mechanism.

2. The prosthetic device of claim 1, wherein the commissure attachment member has a substantially sinusoidal shape.

3. The prosthetic device of claim 1, the commissure attachment member further comprising a latching mechanism movable between an open position and a compressed position, wherein when the latching mechanism is in the open position the commissure attachment member is restrained from movement relative to the expansion and locking mechanism.

4. The prosthetic device of claim 3, wherein the latching mechanism comprises a first member coupled to a second member via a compliant joint, the first and second members being pivotable relative to one another to move the latching mechanism between the open position and the compressed position.

5. The prosthetic device of claim 4, wherein the compliant joint is configured to bias the latching mechanism into the open position.

6. The prosthetic device of claim 1, wherein the first and second lateral extensions are a first set of lateral extensions and the member further comprises a second set of lateral extensions each having an inner bore; and the first and second arm portions are a first set of arm portions and the commissure attachment member further comprises a second set of arm portions each extending into a respective inner bore of the second set of lateral extensions such that the commissure attachment member is restrained from movement relative to the expansion and locking mechanism in the radial and axial directions.

7. The prosthetic device of claim 1, wherein each arm portion comprises a laterally extending portion and an axially extending portion.

8. The prosthetic device of claim 7, wherein the axially extending portions extend toward the inflow end portion of the frame.

9. The prosthetic device of claim 7, wherein the axially extending portions of the arms of the first set of arms extends toward the inflow end portion of the frame, and wherein the axially extending portions of the arms of the second set of arms extends toward the outflow end portion of the frame.

10. The prosthetic device of claim 1, wherein the commissure attachment member has a body portion including two side members defining a commissure opening between them.

11. The prosthetic device of claim 1, further comprising a valvular structure including a plurality of leaflets each having opposing tabs, wherein each pair of adjacent tabs is coupled to a respective expansion and locking mechanism via a respective commissure attachment member.

12. The prosthetic device of claim 11, wherein each tab extends through a commissure opening in the commissure attachment member to form a first layer, folds back along its own respective length to form a second layer and extends around a side portion of the commissure attachment member to form a third layer.

13. The prosthetic device of claim 1, wherein the commissure attachment member has an overall curved shape such that the first and second arm portions curve radially outwardly relative to a body portion.

14. An implantable prosthetic device, comprising:

a radially expandable and compressible frame, the frame comprising an inflow end portion, an outflow end portion, and a commissure post comprising a first set of lateral extensions disposed adjacent an outflow end of the commissure post and a second set of lateral extensions spaced apart from the first set, each lateral extension comprising an inner bore;

a commissure attachment member having a first set of arms each extending into a respective inner bore of a lateral extension of the first set of lateral extensions and a second set of arms each extending into a respective inner bore of a lateral extension of the second set of lateral extensions such that the commissure attachment member is restrained from movement relative to the commissure post in the radial and axial directions; and wherein the commissure attachment member is configured to couple a portion of a valvular structure to the commissure post.

15. The prosthetic device of claim 14, wherein each arm of the first and second sets of arms comprises a laterally extending portion and an axially extending portion.

16. The prosthetic device of claim 14, wherein the axially extending portions extend toward the inflow end portion of the frame.

17. The prosthetic device of claim 14, wherein the axially extending portions of the arms of the first set of arms extends toward the inflow end portion of the frame, and wherein the axially extending portions of the arms of the second set of arms extends toward the outflow end portion of the frame.

\* \* \* \* \*